(12) United States Patent
Fukuma et al.

(10) Patent No.: US 9,962,257 B2
(45) Date of Patent: May 8, 2018

(54) INTRAOCULAR LENS SYSTEM

(71) Applicant: KABUSHIKI KAISHA TOPCON, Tokyo (JP)

(72) Inventors: Yasufumi Fukuma, Wako (JP); Hisashi Tsukada, Hachioji (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 10 days.

(21) Appl. No.: 14/914,457

(22) PCT Filed: Jul. 29, 2014

(86) PCT No.: PCT/JP2014/069926
§ 371 (c)(1),
(2) Date: Feb. 25, 2016

(87) PCT Pub. No.: WO2015/040957
PCT Pub. Date: Mar. 26, 2015

(65) Prior Publication Data
US 2016/0213464 A1 Jul. 28, 2016

(30) Foreign Application Priority Data
Sep. 18, 2013 (JP) .................................. 2013-193464

(51) Int. Cl.
*A61F 2/16* (2006.01)
(52) U.S. Cl.
CPC .......... *A61F 2/1624* (2013.01); *A61F 2/1613* (2013.01); *A61F 2/1648* (2013.01); *A61F 2250/0001* (2013.01)

(58) Field of Classification Search
CPC .... A61F 2/1613; A61F 2/1624; A61F 2/1635; A61F 2/1648
See application file for complete search history.

(56) References Cited

U.S. PATENT DOCUMENTS 6,427,087 B1 7/2002 Chow
2004/0181265 A1 9/2004 Palanker et al.
(Continued)

FOREIGN PATENT DOCUMENTS

JP 2003-190193 7/2003
JP 2003-531697 10/2003
(Continued)

OTHER PUBLICATIONS

Mitsunaga, S., et al., Organic Thin-Film Solar Cell Technologies for Realization of Low-Cost and High-Performance Solar Cells, Toshiba Review, 67(1), 2012, p. 30-33.
(Continued)

*Primary Examiner* — Howie Matthews
(74) *Attorney, Agent, or Firm* — Procopio, Cory, Hargreaves & Savitch LLP

(57) ABSTRACT

An intraocular lens system according to an embodiment includes a lens, a converter, and a driver. The lens is placed in the lens capsule, and configured to allow at least changes of the focal length. The converter is placed in the lens capsule, transmits part of incident light therethrough, and converts the energy of other part of the light into electrical energy. The driver is placed in the lens capsule, operates with the electrical energy obtained by the converter, and is used to change the focal length of the lens.

9 Claims, 12 Drawing Sheets

(56) References Cited

U.S. PATENT DOCUMENTS

| | | | |
|---|---|---|---|
| 2006/0095128 A1 | 5/2006 | Blum et al. | |
| 2008/0046076 A1 | 2/2008 | Rombach | |
| 2008/0208335 A1 | 8/2008 | Blum et al. | |
| 2010/0094413 A1 | 4/2010 | Rombach et al. | |
| 2012/0092612 A1* | 4/2012 | Binder | A61F 2/1613 351/159.02 |
| 2012/0239144 A1 | 9/2012 | Azar | |
| 2013/0282119 A1 | 10/2013 | Pagani | |

FOREIGN PATENT DOCUMENTS

| | | |
|---|---|---|
| JP | 2006-517828 | 8/2006 |
| JP | 2007-526077 | 9/2007 |
| JP | 2010-512814 | 4/2010 |
| JP | 2010-517081 | 5/2010 |
| JP | 2012-130712 | 7/2012 |
| WO | 2012090188 A1 | 7/2012 |

OTHER PUBLICATIONS

International Search Report for PCT/JP2014/069926 dated Sep. 2, 2014, 5 pgs.
English Translation of the Notification of Reasons for Refusal for Japanese Patent Application No. 2013-193464, 7 pages.

\* cited by examiner

INTRAOCULAR LENS SYSTEM

CROSS-REFERENCE TO RELATED APPLICATIONS

This application is U.S. National Stage Application of International Application Ser. No. PCT/JP2014/069926, filed Jul. 29, 2014 which claims benefit of priority from Japanese Patent Application Ser. No. 2013-193464, filed Sep. 18, 2013, the contents of which are incorporated by reference.

TECHNICAL FIELD

Embodiments described herein relate generally to an intraocular lens system including a lens placed in the eye.

BACKGROUND ART

Vision is one of the human senses which has a substantial impact on the quality of life (QOL), and disorders thereof significantly impair the QOL. Therefore, for those having vision disorders, there is a need for the establishment of a technology to complement the lost function. As such a technology, an intraocular lens (IOL), a retinal prosthesis, and the like are known.

Patent Document 1 discloses an intraocular lens which can be placed in the lens capsule (lenticular capsule) inside the eye. The intraocular lens includes an optical unit having a predetermined refractive power and a pair of flat plate-shaped support parts extending from the outer periphery in the vertical direction of the optical unit. The support parts are each provided with a peripheral portion at their ends. The peripheral portion has a peripheral surface for receiving a force applied from the outer circumference of the lens capsule. With this, the optical unit can be displaceable in the optical axis direction according to a force from the outer circumferential direction of the lens capsule due to the movement of the ciliary body (ciliary muscle). Thus, the distance in the visual field can be adjusted.

Patent Document 2 discloses a retinal prosthesis which is implanted inside the eye having a retina. The retinal prosthesis includes a stimulus array arranged in the central region of the retina, and a photovoltaic cell located in the outside of the macular area of the retina or the like. The photovoltaic cell generates electrical power in response to ambient light. The stimulus array utilizes the electrical power generated by the photovoltaic cell.

[Patent Document 1] Japanese Unexamined Patent Application Publication No. 2003-190193

[Patent Document 2] Japanese Unexamined Patent Application Publication (Translation of PCT Application) No. 2006-517828

SUMMARY OF THE INVENTION

Problems to be Solved by the Invention

With the technologies disclosed in Patent Documents 1 and 2, however, if the movement of the ciliary body has become insufficient due to aging or the like, the movement does not act well on the crystalline lens. As a result, the focal length (refractive power) cannot be changed appropriately.

The present invention has been made to solve the above problem, and one object thereof is to provide a technology capable of appropriately changing the focal length of a lens placed in the eye, even if the movement of the ciliary body is insufficient due aging or the like.

Means of Solving the Problems

An intraocular lens system of an embodiment includes: a lens configured to be placed in the lens capsule, and at least have a variable focal length; a converter configured to be placed in the lens capsule, and transmit part of incident light therethrough while converting the energy of other part of the light into electrical energy; and a driver configured to be placed in the lens capsule, and operate with the electrical energy obtained by the converter to change the focal length of the lens.

MODES FOR CARRYING OUT THE INVENTION

A description is given in detail of an intraocular lens system according to exemplary embodiments with reference to the accompanying drawings. The intraocular lens system of an embodiment includes a lens, which is configured to be placed within the eye, and the focal length (focal point) of which is variable. The focal length of the lens is changed in response to electrical energy converted from the energy of light incident on the eye. The disclosure of the references cited in this specification may be incorporated herein by reference.

<First Embodiment>
[Configuration]

Figure 1:
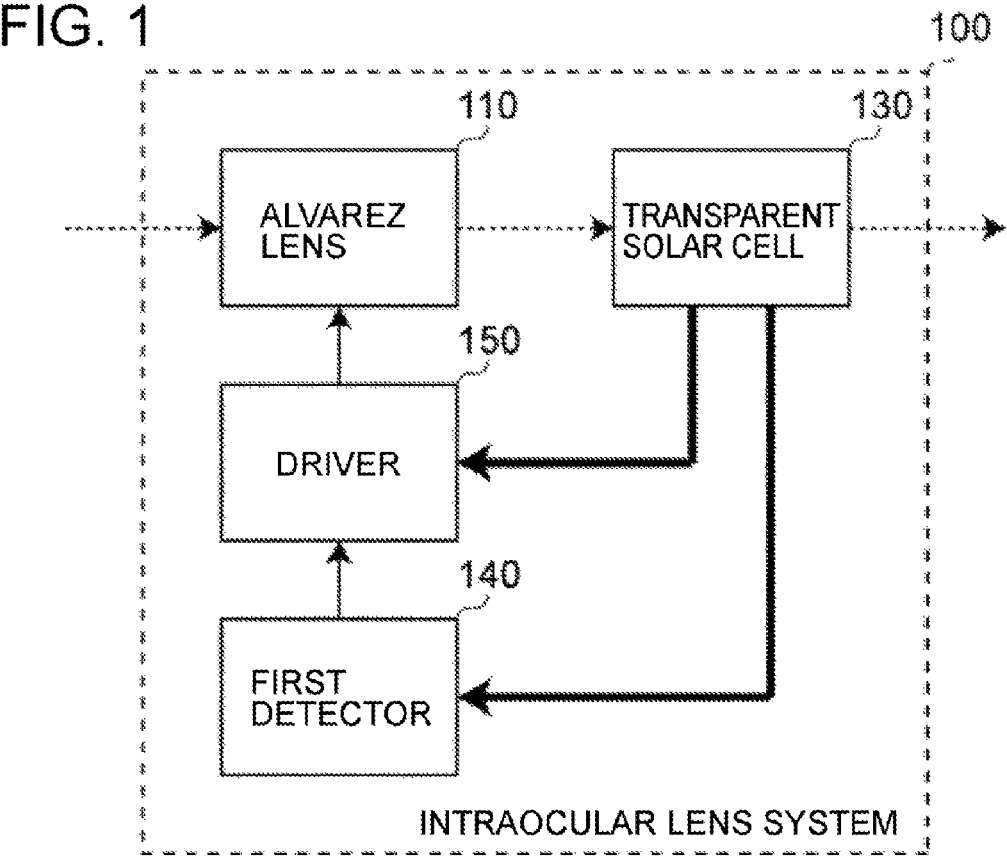
FIG. 1 is a schematic diagram illustrating an example of the configuration of an intraocular lens system according to an embodiment.

FIG. 1 is a functional block diagram illustrating an example of the configuration of an intraocular lens (IOL) system according to a first embodiment. An intraocular lens system 100 includes an Alvarez lens 110, a transparent solar cell 130, a first detector 140, and a driver 150. The intraocular lens system 100 is, for example, placed inside the lens capsule from which the crystalline lens has been removed by known phacoemulsification. In FIG. 1, the path of light is indicated by a broken arrow in distinction from the paths of others (e.g., electrical signal, etc.) each indicated by a solid line.

The Alvarez lens 110 is a variable focus lens, at least the focal length of which can be changed. The transparent solar cell 130 transmits part of the light incident on the eye (lens capsule) therethrough, and converts the energy of other part into electrical energy. The first detector 140 detects the movement of the ciliary body or a biological signal for moving the ciliary body. Examples of the biological signal for moving the ciliary body include a signal sent from the brain to the ciliary body through the nerves. When the external power supply is required, the first detector 140 operates by receiving the electrical energy obtained by the transparent solar cell 130. The driver 150 operates by receiving the electrical energy generated by the transparent solar cell 130 to change the focal length of the Alvarez lens 110 based on the detection result obtained by the first detector 140. In this embodiment, the first detector 140 and the driver 150 are constituted by hardware (circuits, etc.) to use the detection result obtained by the first detector 140 as a drive control signal for controlling the driver 150. The term "pass" as used herein includes the meaning of "transmit", and "pass" and "transmit" may be used as the same meaning. Further, the terms "electrical energy" and "electrical power" as used herein may be deemed to be the same.

A power supply line is provided between the transparent solar cell 130 and the first detector 140 to supply the electric power (electrical energy) generated by the transparent solar cell 130. In addition, a power supply line is provided between the transparent solar cell 130 and the driver 150 to supply the electric power generated by the transparent solar cell 130. Besides, a signal line is provided between the first detector 140 and the driver 150 to supply a drive signal for driving the driver 150.

In this embodiment, in the lens capsule, the Alvarez lens 110 transmits light incident on the eye, and the transparent solar cell 130 converts the energy of the light having transmitted through the Alvarez lens 110 into electrical energy. That is, the Alvarez lens 110 is placed on the cornea side, while the transparent solar cell 130 is placed on the fundus side.

(Alvarez Lens and Driver)

The Alvarez lens 110 includes a pair of optical elements 111 and 112, and its spherical power can be changed by the relative movement of the optical elements 111 and 112. In other words, the focal length of the Alvarez lens 110 is changed by the relative movement of the optical elements 111 and 112.

Figure 2:
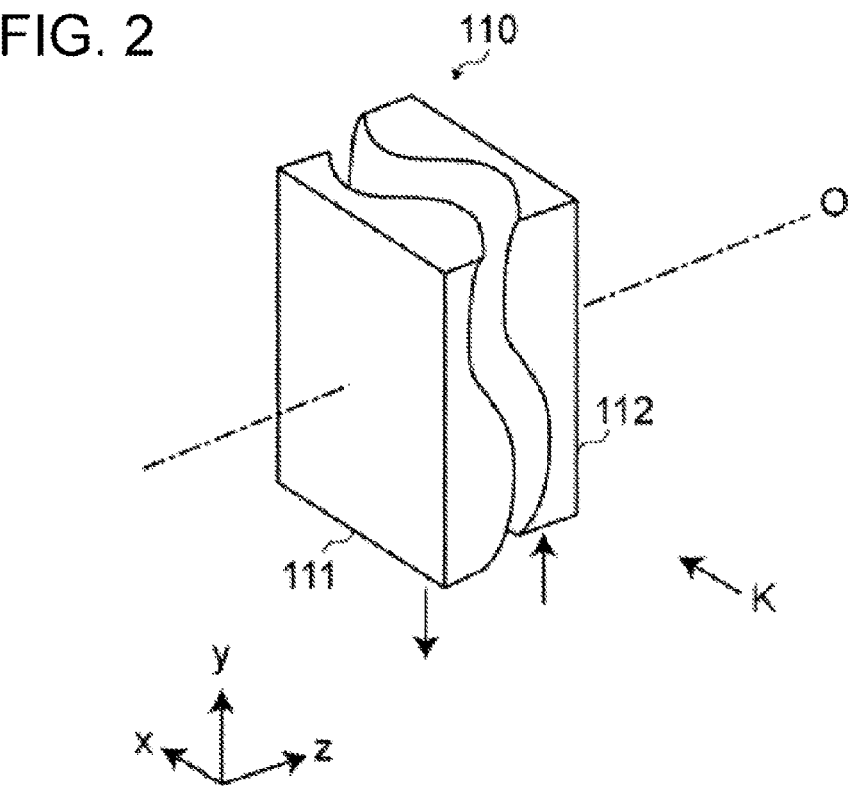
FIG. 2 is a schematic diagram illustrating an example of the configuration of an intraocular lens system according to an embodiment.

FIG. 2 is an explanatory diagram of the Alvarez lens 110 of the first embodiment. In FIG. 2, the horizontal direction is defined as x direction, the vertical direction is defined as y direction, and the direction toward the fundus is defined as z direction. The optical elements 111 and 112 are placed on a predetermined axis O of the Alvarez lens 110. The surfaces of the optical elements 111 and 112 facing each other have a shape of a known three-dimensional curved surface.

A direction parallel to the axis O is defined as the z direction. By relatively moving the optical elements 111 and 112 in the y direction (vertical direction) within the xy plane perpendicular to the axis O (see FIG. 2), the refractive power (spherical power) obtained by optically combining the optical elements 111 and 112 can be continuously changed. In FIG. 2, the optical element 111 is moved downward (−y direction), and the optical element 112 is moved upward (+y direction).

Figure 3:
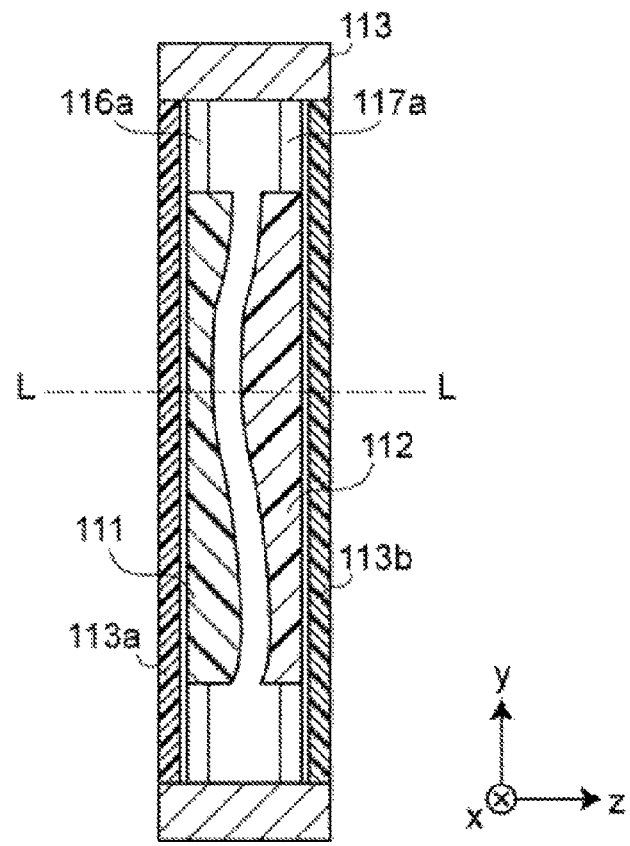
FIG. 3 is a schematic diagram illustrating an example of the configuration of an intraocular lens system according to an embodiment.
Figure 4:
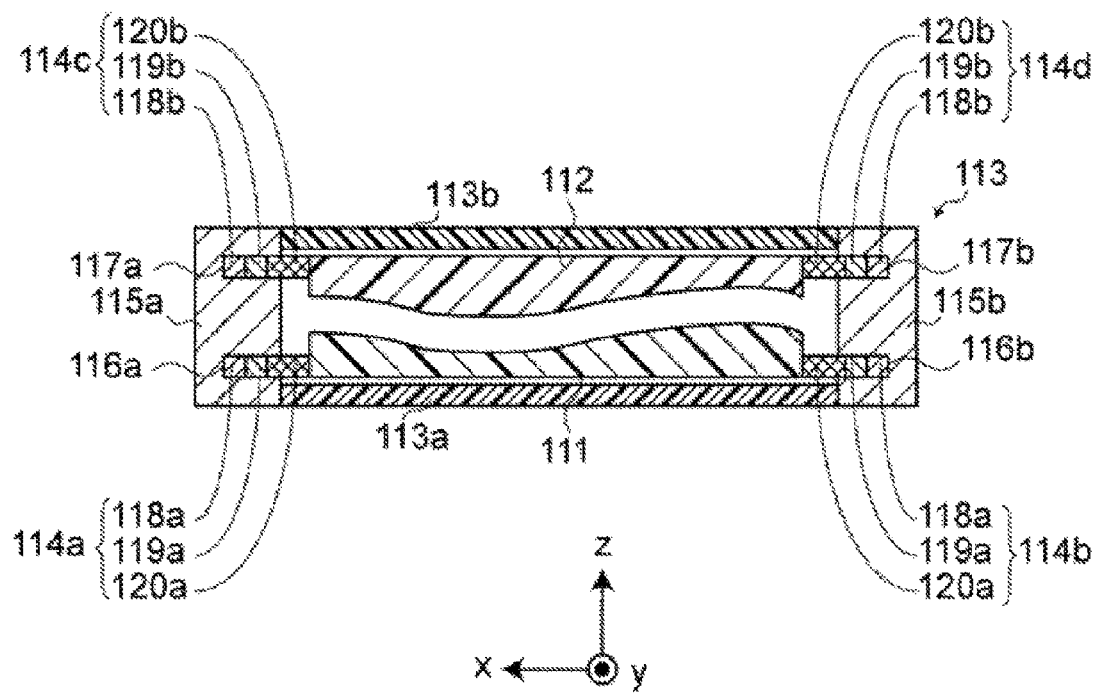
FIG. 4 is a schematic diagram illustrating an example of the configuration of an intraocular lens system according to an embodiment.

FIGS. 3 and 4 illustrate examples of cross-sections of the Alvarez lens 110 of the first embodiment. FIG. 3 is a schematic vertical cross-sectional view, passing through the axis O, of the Alvarez lens 110 of FIG. 2 as viewed from the K direction. FIG. 4 is a cross-sectional view taken along a line L-L in FIG. 3.

The optical elements 111 and 112, which constitute the Alvarez lens 110, are housed in an envelope 113 filled with a medium such as air having a predetermined transmittance. This medium need not necessarily be air but may be a gas other than air, a liquid, or a solid having a viscosity. The envelope 113 is provided with a transparent member 113a that transmits the light from the first main surface side (outside) to the inside of the envelope 113, and a transparent member 113b that transmits the light inside the envelope 113 to the second main surface side (in the eye), which is the opposite of the first main surface. The optical elements 111 and 112 are located between the transparent members 113a and 113b in the envelope 113.

Ultrasonic linear motors 114a to 114d are provided inside the envelope 113. The ultrasonic linear motors 114a to 114d relatively move the optical elements 111 and 112 in the vertical direction (y direction in FIG. 2). In this embodiment, the ultrasonic linear motors 114a to 114d constitute the driver 150.

The envelope 113 is provided with side walls 115a and 115b on the left and right sides. The side wall 115a has guide grooves 116a and 117a formed to extend vertically. The side wall 115b has guide grooves 116b and 117b formed to extend vertically correspondingly to the vertical guide grooves 116a and 117a. The ultrasonic linear motor 114a is provided in the guide groove 116a. The ultrasonic linear motor 114b is provided in the guide groove 116b.

The ultrasonic linear motors 114a and 114b each include a piezoelectric element array 118a, a vibrator 119a as a stator, and a mover 120a. The piezoelectric element array 118a is formed, for example, in a straight line by connecting electrodes and piezoelectric elements alternately. The vibrator 119a includes, for example, a number of teeth arranged in the longitudinal direction on the opposite side to the piezoelectric element array 118a, and is driven to vibrate by the piezoelectric element array 118a. The mover 120a is engaged with the teeth of the vibrator 119a by friction. The piezoelectric element array 118a is fixed to the vibrator 119a. The movers 120a and 120b of the guide grooves 116a and 116b are fixed on both sides of the optical element 111.

Similarly, the ultrasonic linear motor 114c is provided in the guide groove 117a and the ultrasonic linear motor 114d is provided in the guide groove 117b.

The ultrasonic linear motors 114c and 114d each include a piezoelectric element array 118b, a vibrator 119b as a stator, and a mover 120b. The piezoelectric element array 118b is formed, for example, in a straight line by connecting electrodes and piezoelectric elements alternately. The vibrator 119a includes, for example, a number of teeth arranged in the longitudinal direction on the opposite side to the piezoelectric element array 118b, and is driven to vibrate by the piezoelectric element array 118b. The mover 120b is engaged with the teeth of the vibrator 119b by friction. The piezoelectric element array 118b is fixed to the vibrator 119b. The movers 120b, 120b of the guide grooves 117a and 117b are fixed on both sides of the optical element 112.

In the configuration illustrated in FIGS. 3 and 4, the voltage applied to the electrodes of the piezoelectric element array 118a is controlled to change the phase of bending standing wave vibration generated on the teeth side of the vibrator 119a. Thereby, the vibrator 119a moves the mover 120a up or down. The ultrasonic linear motors 114a and 114b may have the structure of a known ultrasonic linear motor.

Similarly, the voltage applied to the electrodes of the piezoelectric element array 118b is controlled to change the phase of bending standing wave vibration generated on the teeth side of the vibrator 119b. Thereby, the vibrator 119b moves the mover 120b up or down. The ultrasonic linear motors 114c and 114d may have the structure of a known ultrasonic linear motor.

With the above configuration, the ultrasonic linear motors 114a to 114d move the optical elements 111 and 112 vertically, and thereby the Alvarez lens 110 is set to have a desired spherical power. Incidentally, the Alvarez lens 110 having the structure described above may be sealed in a package of a predetermined shape so that it can be easily inserted into the lens capsule and held therein. The Alvarez lens 110 is an example of the "lens". The driver 150 is an example of the "driver".

(Transparent Solar Cell)

The transparent solar cell 130 is formed using, for example, the organic thin film technology.

Figure 5:
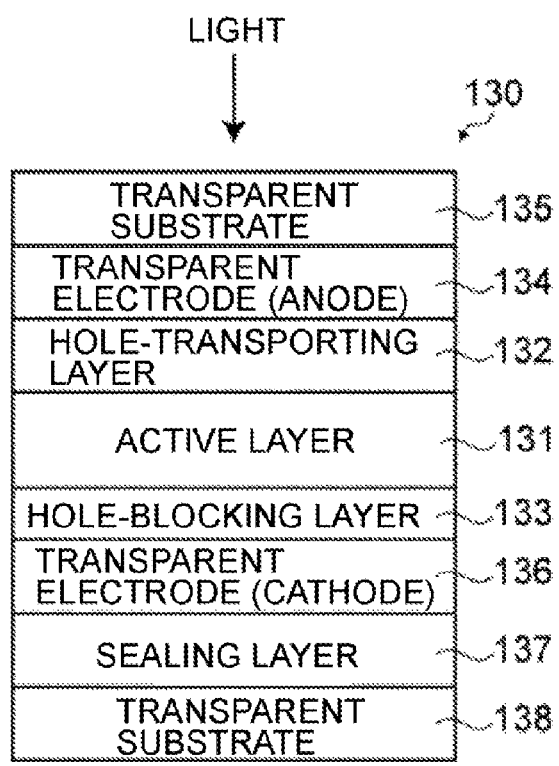
FIG. 5 is a schematic diagram illustrating an example of the configuration of an intraocular lens system according to an embodiment.

FIG. 5 schematically illustrates an example of the sectional structure of the transparent solar cell 130 of the first embodiment. The transparent solar cell 130 has a structure in which an active layer 131 for generating electric power by receiving light is sandwiched between a hole transport layer 132 and a hole block layer 133. The hole transport layer 132 is formed on the light-receiving surface side with respect to the active layer 131. The hole block layer 133 is formed on the side opposite the hole transport layer 132 with respect to the active layer 131. A transparent electrode 134 serving as an anode is formed on the light-receiving surface side of the hole transport layer 132. A transparent substrate 135 is arranged on the light-receiving surface side of the transparent electrode 134. Meanwhile, a transparent electrode 136 as a cathode is formed on the side opposite to the light receiving surface of the hole block layer 133. The element including the transparent substrate 135, the transparent electrode 134, the hole transport layer 132, the active layer 131, the hole block layer 133, and the transparent electrode 136 is sealed by a sealing layer 137 made of a transparent epoxy resin and a transparent substrate 138.

The active layer 131 can be formed by dissolving a p-type organic semiconductor and an n-type organic semiconductor in an organic solvent, and applying it by spin coating. The active layer 131 thus formed has a bulk heterojunction structure. The light incident on the transparent solar cell 130 is absorbed in the active layer 131. In the active layer 131, excitons are generated by photoexcitation in the n-type organic semiconductor, for example. The excitons are diffused in the n-type organic semiconductor. The excitons diffused to the p-n junction interface are dissociated into holes and electrons. The holes are dispersed in the p-type organic semiconductor, and are transported through the hole transport layer 132 to the transparent electrode 134. Meanwhile, the electrons are dispersed in the n-type organic semiconductor, and are transported through the hole block layer 133 to the transparent electrode 136. As a result, a potential difference is generated between the transparent electrode 134 and the transparent electrode 136.

The hole transport layer 132 suppresses the deactivation caused by the recombination of holes and electrons resulted from the movement of the holes and the electrons to the anode side. The hole block layer 133 suppresses the deactivation caused by the recombination of holes and electrons resulted from the movement of the holes and the electrons to the cathode side.

For more information about a technology related to a cell such as the transparent solar cell 130, reference may be had to, for example, "Organic Thin-Film Solar Cell Technologies for Realization of Low-Cost and High-Performance Solar Cells" (Saito Mitsunaga et al., Toshiba Review, Vol. 67 No. 1 (2012), p. 30-33).

With the configuration described above, the transparent solar cell 130 can transmit part of the light incident on the crystalline lens therethrough, and convert the energy of other part into electrical energy. As described below, by forming an opening, the transparent solar cell 130 can transmit part of the light incident on the lens capsule therethrough, and convert the energy of other part of the light into electrical energy. The transparent solar cell 130 is an example of the "converter".

(First Detector)

The focal length of the eye is changed by changing the thickness of the crystalline lens enclosed within the lens capsule. The thickness of the crystalline lens varies depending on the movement of the ciliary body, which is transmitted to the lens capsule through the ciliary zonule (zonule of Zinn). The first detector 140 may be configured to detect at least one of the acceleration of a predetermined portion of the ciliary body which functions to change the thickness of the crystalline lens, the movement amount of a predetermined portion of the ciliary body, the tension of the ciliary zonule, pressure in the lens capsule, and a myoelectric potential signal of the ciliary body.

When used to detect an acceleration of a predetermined portion of the ciliary body, the first detector 140 includes an acceleration sensor or the like attached to the predetermined portion of the ciliary body. In this case, the first detector 140 outputs a drive signal corresponding to the detected acceleration to the driver 150. For example, the first detector 140 is configured to output a drive signal having a predetermined relationship to the detected acceleration. Thus, even if the movement of the ciliary body becomes insufficient due to its weakening, the first detector 140 can output a drive signal obtained by amplifying the movement of the ciliary body. Besides, to respond to the characteristics of the eye where it is placed and further weakening of the ciliary body afterwards, for example, the first detector 140 may refer to table information that associates acceleration values with drive signals (amplitudes, phases, or the like), and output a drive signal associated with the detected acceleration to the driver 150. In this case, the table information is changeable (the same applies to the following).

When used to detect the movement amount of a predetermined portion of the ciliary body, the first detector 140 includes a position sensor or the like attached to the predetermined portion of the ciliary body. In this case, the first detector 140 outputs a drive signal corresponding to the detected movement amount to the driver 150. For example, the first detector 140 is configured to output a drive signal having a predetermined relationship to the detected movement amount. Thus, even if the movement of the ciliary body becomes insufficient due to its weakening, the first detector 140 can output a drive signal obtained by amplifying the movement of the ciliary body. Besides, to respond to the characteristics of the eye where it is placed and further weakening of the ciliary body afterwards, for example, the first detector 140 may refer to table information that associates movement amounts with drive signals (amplitudes, phases, or the like), and output a drive signal associated with the detected movement amount to the driver 150.

When used to detect the tension of the ciliary zonule, the first detector 140 includes a tension sensor or the like attached to the ciliary zonule. In this case, the first detector 140 outputs a drive signal corresponding to the detected tension to the driver 150. For example, the first detector 140 is configured to output a drive signal having a predetermined relationship to the detected tension. Thus, even if the movement of the ciliary body becomes insufficient due to its weakening, the first detector 140 can output a drive signal obtained by amplifying the movement of the ciliary body. Besides, to respond to the characteristics of the eye where it is placed and further weakening of the ciliary body afterwards, for example, the first detector 140 may refer to table information that associates tension values with drive signals (amplitudes, phase, or the like), and output a drive signal associated with the detected tension to the driver 150.

When used to detect the pressure in the lens capsule, the first detector 140 includes a pressure sensor or the like attached to the lens capsule. In this case, the first detector 140 outputs a drive signal corresponding to the detected pressure to the driver 150. For example, the first detector 140 is configured to output a drive signal having a predetermined relationship to the detected pressure. Thus, even if the movement of the ciliary body becomes insufficient due to its weakening, the first detector 140 can output a drive signal obtained by amplifying the movement of the ciliary body. Besides, to respond to the characteristics of the eye where it is placed and further weakening of the ciliary body afterwards, for example, the first detector 140 may refer to table information that associates pressure values with drive signals (amplitudes, phase, or the like), and output a drive signal associated with the detected pressure in the lens capsule to the driver 150.

When used to detect a myoelectric potential signal (in a broader sense, a biological signal) of a predetermined portion of the ciliary body, the first detector 140 includes a myoelectric potential sensor or the like attached to the predetermined portion of the ciliary body. In this case, the first detector 140 outputs a drive signal corresponding to the detected myoelectric potential signal to the driver 150. For example, the first detector 140 is configured to output a drive signal having a predetermined relationship to the detected myoelectric potential signal. Thus, even if the movement of the ciliary body becomes insufficient due to its weakening, the first detector 140 can output a drive signal obtained by amplifying the movement of the ciliary body. Besides, to respond to the characteristics of the eye where it is placed and further weakening of the ciliary body afterwards, for example, the first detector 140 may refer to table information that associates the myoelectric potential signals with drive signals (amplitudes, phases, or the like), and output a drive signal associated with the detected myoelectric potential signal to the driver 150.

The first detector 140 may be configured by using any one of the above sensors, or may be configured to output a drive signal corresponding to the combination of detection results obtained by at least two of the above sensors to the driver 150.

With the above configuration, the first detector 140 detects the movement of the ciliary body or a biological signal for moving the ciliary body, and outputs a drive signal corresponding to the detection result to the driver 150. The driver 150 changes the focal length of the Alvarez lens 110 based on the drive signal corresponding to the detection result obtained by the first detector 140. At this time, the first detector 140 can output a drive signal by amplifying the movement of the ciliary body to the driver 150. Thus, even when the movement of the ciliary body is insufficient due to aging or the like, the driver 150 can be driven to properly change the focal length of the Alvarez lens 110. Note that the first detector 140 may include a sensor that needs no power supply from the transparent solar cell 130. In this case, there is no need of the power supply line connecting the transparent solar cell 130 with the first detector 140. The first detector 140 is an example of the "first detector".

[Arrangement Example]

Figure 6:
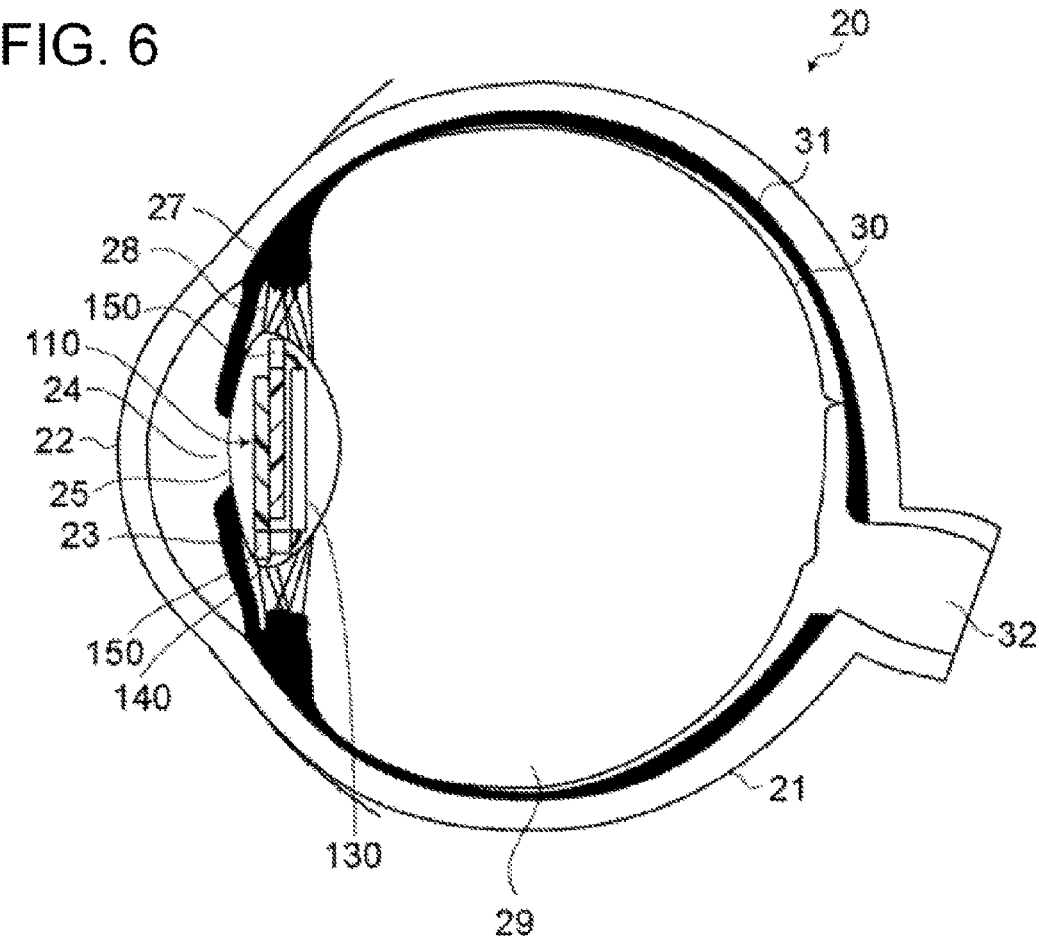
FIG. 6 is a schematic diagram illustrating an example of the configuration of an intraocular lens system according to an embodiment.

FIG. 6 is a schematic cross-sectional view of an eye in which the intraocular lens system 100 of the first embodiment is placed. Specifically, FIG. 6 is a cross sectional view of the right eye as viewed from the above. Like reference numerals designate like parts as in FIG. 1, and the same description may not be repeated. For convenience of explanation, FIG. 6 may not illustrate power lines and signal lines which connect parts of the intraocular lens system 100.

An eye 20 has a substantially spherical shape and the outer is covered by a sclera 21. The light incident from the front of the eye 20 is refracted by a cornea 22, and passes through a pupil 24, whose size has been adjusted by an iris 23. As the light is passing through the pupil 24, the amount of light projected on a retina 30 is adjusted. The light having passed through the pupil 24 is refracted again by the intraocular lens system 100 arranged in a lens capsule 25.

The intraocular lens system 100 can detect, by the first detector 140, the movement (tensed or relaxed state, etc.) of a ciliary body 27 transmitted to the lens capsule through a ciliary zonule 28. In the intraocular lens system 100, the focal length of the Alvarez lens 110 is changed based on the detection result obtained by the first detector 140. The light having transmitted through the Alvarez lens 110 is incident on the transparent solar cell 130. The transparent solar cell 130 transmits part of the light having transmitted through the Alvarez lens 110, and converts the energy of other part into electrical energy. The electrical energy obtained by the transparent solar cell 130 is supplied to the first detector 140 and the driver 150.

After having been refracted by the intraocular lens system 100 with the focal length changed in this manner, the light passes through a vitreous body 29 and reaches the retina 30. A choroid 31 supplies oxygen, nutrition, and the like to the retina 30. The retina 30 has a number of photoreceptor cells. The light that has reached the retina 30 is converted by the photoreceptor cells into electrical signals. The electrical signals generated by the photoreceptor cells are collected in the optic nerve head through nerve fibers of the retina 30, and sent to the brain via an optic nerve 32.

[Operation]

Figure 7:
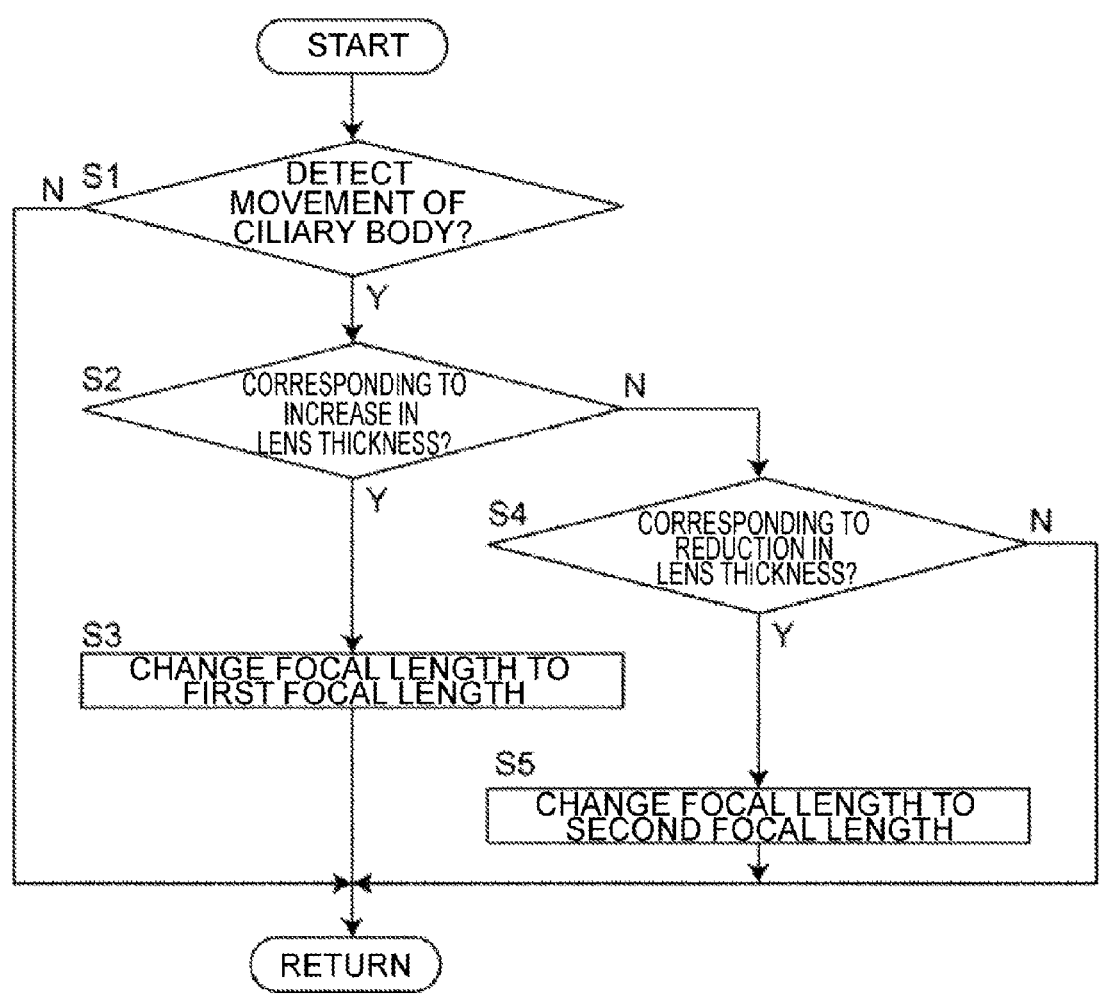
FIG. 7 is a flowchart illustrating an example of the operation of the intraocular lens system of the embodiment.

FIG. 7 is a flowchart of an example of the operation of the intraocular lens system 100 of the first embodiment. With reference to FIG. 7, a description is given of an example in which the first detector 140 detects the movement of the ciliary body 27. Note that the intraocular lens system 100 operates similarly also when the first detector 140 detects a biological signal for moving the ciliary body 27.

(S1: Detect Movement of Ciliary Body?)

First, the first detector 140 monitors the movement of the ciliary body 27. When the movement of the ciliary body 27 is detected (step S1: Y), the process proceeds to step S2. When the movement of the ciliary body 27 is not detected (step S1: N), the intraocular lens system 100 continues the process of step S1 (Return).

(S2: Corresponding to Increase in Lens Thickness? and S3: Change Focal Length to First Focal Length)

When the movement of the ciliary body 27 detected in step S1 is a movement corresponding to an increase in the lens thickness (step S2: Y), the first detector 140 generates a drive signal to change the focal length of the Alvarez lens 110 to a first focal length that is shorter than the current focal length, and outputs the drive signal to the driver 150. At this time, the first detector 140 generates the drive signal that indicates the change amount and change direction of the focal length corresponding to the movement (acceleration, etc.) of the ciliary body 27 detected in step S1.

(S4: Corresponding to Reduction in Lens Thickness? and S5: Change Focal Length to Second Focal Length)

When the movement of the ciliary body 27 detected in step S1 is a movement corresponding to a reduction in the lens thickness (step S2: N, step S4: Y), the first detector 140 generates a drive signal to change the focal length of the Alvarez lens 110 to a second focal length that is longer than the current focal length, and outputs the drive signal to the driver 150. At this time, the first detector 140 generates the drive signal to change the focal length according to the movement (acceleration, etc.) of the ciliary body 27 detected in step S1.

After step S3 or step S5, the process loops back to step S1 (Return). Similarly, when the movement of the ciliary body 27 detected in step S1 is neither a movement corresponding to an increase nor a reduction in the lens thickness (step S4: N), the process loops back to step S1 (Return). For example, if the detection result obtained by the first detector 140 is less than a threshold, the process moves from step S4 to step S1. The threshold can be changed afterwards. Further, in addition to the first detector 140, there may be provided a means for detecting the eye movement. In this case, based on the detection results obtained by the first detector 140 and the means, information on the eye movement is canceled from the detection result obtained by the first detector 140 to thereby extract information substantially required to change the thickness of the crystalline lens.

As described above, in the intraocular lens system 100 of this embodiment, when the first detector 140 detects the movement of the ciliary body 27 corresponding to an increase in the lens thickness, the Alvarez lens 110 is driven such that the focal length becomes shorter according to the movement detected. On the other hand, when the first detector 140 detects the movement of the ciliary body 27 corresponding to a reduction in the lens thickness, the Alvarez lens 110 is driven such that the focal length becomes longer according to the movement detected.

Although this embodiment describes an example in which the intraocular lens system 100 is placed in the lens capsule 25, this is not a limitation. It may be sufficient if each part is held or placed in the eye.

[Effects]

The intraocular lens system 100 is an example of the intraocular lens system of this embodiment. Described below are the effects of the intraocular lens system of this embodiment.

The intraocular lens system (e.g., the intraocular lens system 100) includes a lens (e.g., the Alvarez lens 110), a converter (e.g., the transparent solar cell 130), and a driver (e.g., the driver 150).

The lens is placed in the lens capsule, and configured to allow changes of the focal length. The converter is placed in the lens capsule, and configured to transmit part of incident light therethrough and convert the energy of other part of the light into electrical energy. Here, "other part of the light" may include the entire part of the light incident on the lens capsule excluding the part of the light that transmits through the converter. The driver is placed in the lens capsule, and configured to operate with the electrical energy received from the converter to change the focal length of the lens.

In the intraocular lens system, the converter converts the energy of light incident on the eye (lens capsule) into electrical energy. The driver receives the electrical energy obtained by the converter to drive the lens. Thus, the lens can be placed in the lens capsule in a conventional manner. Further, the focal length of the lens can be changed appropriately by using the energy of light incident on the lens capsule.

In the intraocular lens system, the lens may be configured to transmit light incident on the lens capsule therethrough, and the converter may be configured to convert the energy of the light having transmitted through the lens into electrical energy. In the intraocular lens system thus configured, the lens is placed on the cornea side, while the converter is placed on the fundus side. In this manner, the lens and the converter are placed in proximity, which reduces the space required for the placement. Thus, the lens and the converter can be easily placed in the lens capsule.

In the intraocular lens system, a first detector (e.g., the first detector 140) may be placed in the lens capsule to detect the movement of the ciliary body or a biological signal for moving the ciliary body. Further, the driver may be configured to change the focal length of the lens based on the detection result obtained by the first detector.

With the intraocular lens system, since the first detector detects the movement of the ciliary body or a biological signal for moving the ciliary body, the driver can change the focal length of the lens by amplifying the movement of the ciliary body. Thus, even if the movement of the ciliary body is insufficient, the focal length of the lens can be changed appropriately by amplifying the movement of the ciliary body.

In the intraocular lens system, the first detector may be configured to detect at least one of the acceleration of a predetermined portion of the ciliary body, the movement amount of a predetermined portion of the ciliary body, the tension of the ciliary zonule, pressure in the lens capsule, and a myoelectric potential signal of a predetermined portion of the ciliary body.

The movement of the ciliary body leads to a change in the acceleration of the predetermined portion of the ciliary body, the movement amount of the predetermined portion of the ciliary body, the tension of the ciliary zonule, or the myoelectric potential signal of the predetermined portion of the ciliary body. Therefore, the first detector is provided to detect such physical quantities. Thereby, the movement of the ciliary body can be detected with high accuracy. Thus, the lens can be controlled to be driven with high accuracy according to the movement of the ciliary body.

In addition, the intraocular lens system may include a transparent solar cell configured to transmit part of light incident on the eye therethrough and convert the energy of other part into electrical energy.

The transparent solar cell transmits light incident on the eye. The light having transmitted through the transparent solar cell reaches the retina. With this, it becomes possible to secure the size of the light receiving surface of the transparent solar cell without blocking the light to reach the retina. Thus, it is possible to generate more electrical power without blocking the light to reach the retina.

In the intraocular lens system, the lens may be configured to allow a continuous change of the focal length. With the intraocular lens system, the focal length can be finely changed according to the movement of the ciliary body. Note that the lens may be configured to allow changes of the focal length step by step. The step can be changed afterwards.

In the intraocular lens system, the lens may include an Alvarez lens.

With the intraocular lens system, the focal length can be changed with the use of the Alvarez lens by using electrical power generated in the lens capsule.

<Second Embodiment>

In the first embodiment, an example is described in which the Alvarez lens 110 is placed on the cornea side, and the transparent solar cell 130 is placed on the fundus side. However, the transparent solar cell 130 may be placed on the cornea side, and the Alvarez lens 110 may be placed on the fundus side. In the following, an intraocular lens system according to a second embodiment is described focusing on differences from the first embodiment.

[Configuration]

Figure 8:
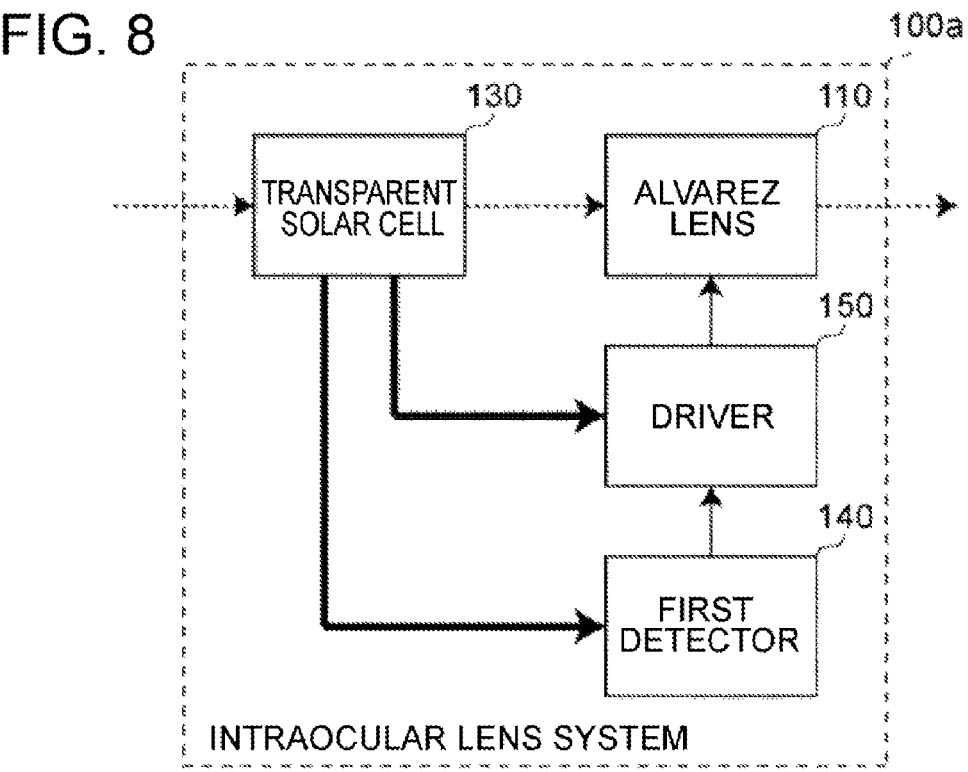
FIG. 8 is a schematic diagram illustrating an example of the configuration of an intraocular lens system according to an embodiment.

FIG. 8 is a functional block diagram illustrating an example of the configuration of an intraocular lens system according to the second embodiment. In FIG. 8, like reference numerals designate like parts as in FIG. 1, and the same description may not be repeated. In FIG. 8, the path of light is indicated by a broken arrow in distinction from the paths of others (e.g., electrical signal, etc.) each indicated by a solid line.

An intraocular lens system 100a includes the Alvarez lens 110, the transparent solar cell 130, the first detector 140, and the driver 150. As with the intraocular lens system 100, the intraocular lens system 100a is placed in the lens capsule. The intraocular lens system 100a is different from the intraocular lens system 100 in that the transparent solar cell 130 is placed on the cornea side, while the Alvarez lens 110 is placed on the fundus side.

In this embodiment, in the lens capsule, the transparent solar cell 130 transmits part of light incident on the eye therethrough, and converts the energy of other part into electrical energy. The Alvarez lens 110 converts the energy of the light having transmitted through the transparent solar cell 130 into electrical energy. That is, the transparent solar cell 130 is placed on the cornea side, while the Alvarez lens 110 is placed on the fundus side.

The Alvarez lens 110, the transparent solar cell 130, the first detector 140, and the driver 150 of the intraocular lens system 100a are the same as those described in the first embodiment, and therefore their explanation is omitted.

[Arrangement Example]

Figure 9:
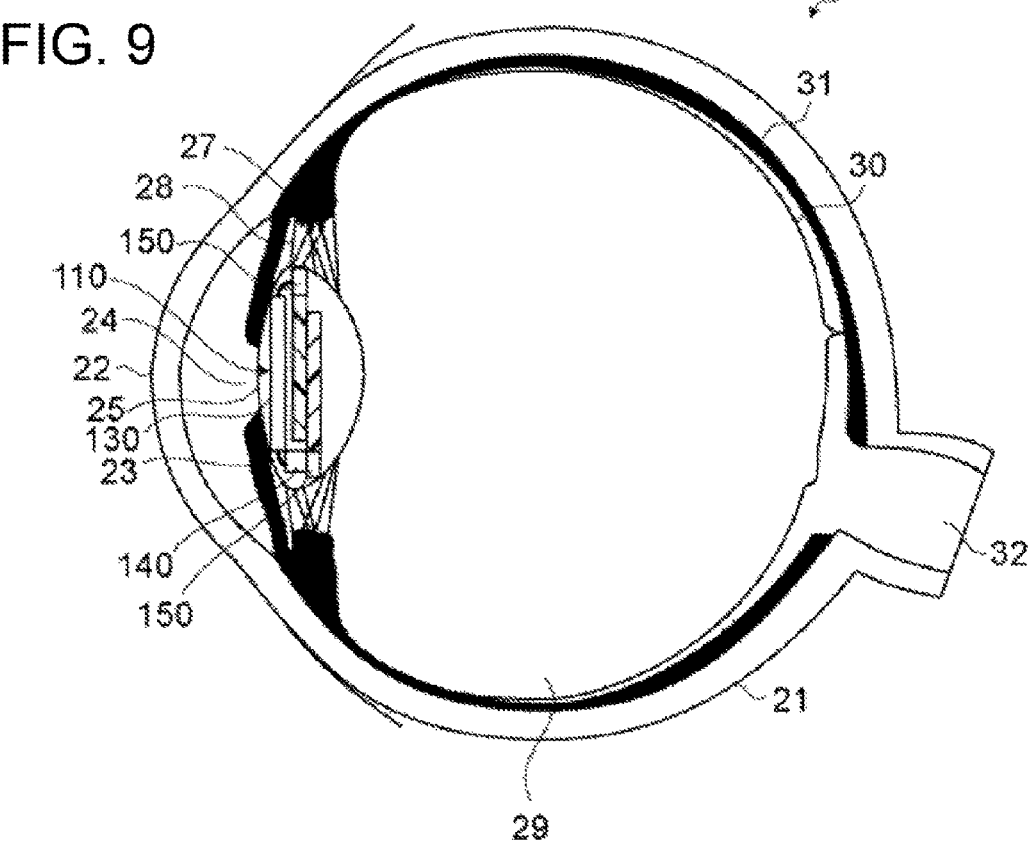
FIG. 9 is a schematic diagram illustrating an example of the configuration of an intraocular lens system according to an embodiment.

FIG. 9 is a schematic cross-sectional view of an eye in which the intraocular lens system 100a of the second embodiment is placed. Specifically, FIG. 9 is a cross sectional view of the right eye as viewed from the above. Like reference numerals designate like parts as in FIG. 8, and the same description may not be repeated. For convenience of explanation, FIG. 9 may not illustrate power lines and signal lines connecting parts of the intraocular lens system 100a.

The eye 20 has a substantially spherical shape and the outer is covered by the sclera 21. The light incident from the front of the eye 20 is refracted by the cornea 22, and passes through the pupil 24, whose size has been adjusted by the iris 23. As the light is passing through the pupil 24, the amount of light projected on the retina 30 is adjusted. The light having passed through the pupil 24 is refracted again by the intraocular lens system 100a arranged in the lens capsule 25.

In the intraocular lens system 100a, the light incident on the lens capsule enters the transparent solar cell 130. The transparent solar cell 130 transmits part of the light incident on the lens capsule therethrough, and converts the energy of other part into electrical energy. The electrical energy obtained by the transparent solar cell 130 is supplied to the first detector 140 and the driver 150.

The intraocular lens system 100a can detect, by the first detector 140, the movement of the ciliary body 27 transmitted to the lens capsule through the ciliary zonule 28. In the intraocular lens system 100a, the focal length of the Alvarez lens 110 is changed based on the detection result obtained by the first detector 140.

After having been refracted by the intraocular lens system 100a with the focal length changed in this manner, the light passes through the vitreous body 29 and reaches the retina 30. The choroid 31 supplies oxygen, nutrition, and the like to the retina 30. The retina 30 has a number of photoreceptor cells. The light that reaches the retina 30 is converted by the photoreceptor cells into electrical signals. The electrical signals obtained by the photoreceptor cells are collected in the optic nerve head through nerve fibers of the retina 30, and sent to the brain via the optic nerve 32.

The intraocular lens system 100a of the second embodiment operates in a similar manner to that of the first embodiment except the difference in the passage (transmission order) of light incident on the lens capsule.

[Effects]

The intraocular lens system 100a is an example of the intraocular lens system of this embodiment. Described below are the effects of the intraocular lens system of this embodiment.

The intraocular lens system (e.g., the intraocular lens system 100a) includes a lens (e.g., the Alvarez lens 110), a converter (e.g., the transparent solar cell 130), and a driver (e.g., the driver 150). The converter is configured to transmit part of light incident on the lens capsule therethrough. The lens is configured to transmit the light that has transmitted through the converter.

In the intraocular lens system, light incident on the eye (lens capsule) enters the converter, and part of the energy of the incident light is converted into electrical energy. The light having transmitted through the converter is incident on the Alvarez lens. The driver receives the electrical energy obtained by the converter to drive the lens. Thus, the lens can be placed in the lens capsule in a conventional manner. Further, the focal length of the lens can be changed appropriately by using the energy of light incident on the lens capsule.

<Third Embodiment>

In the first embodiment and the second embodiment, the converter for converting optical energy into electrical energy is described as being transmissive by way of example. However, the converter may be non-transmissive. In the following, an intraocular lens system according to a third embodiment is described focusing on differences from the first embodiment.

[Configuration]

Figure 10:
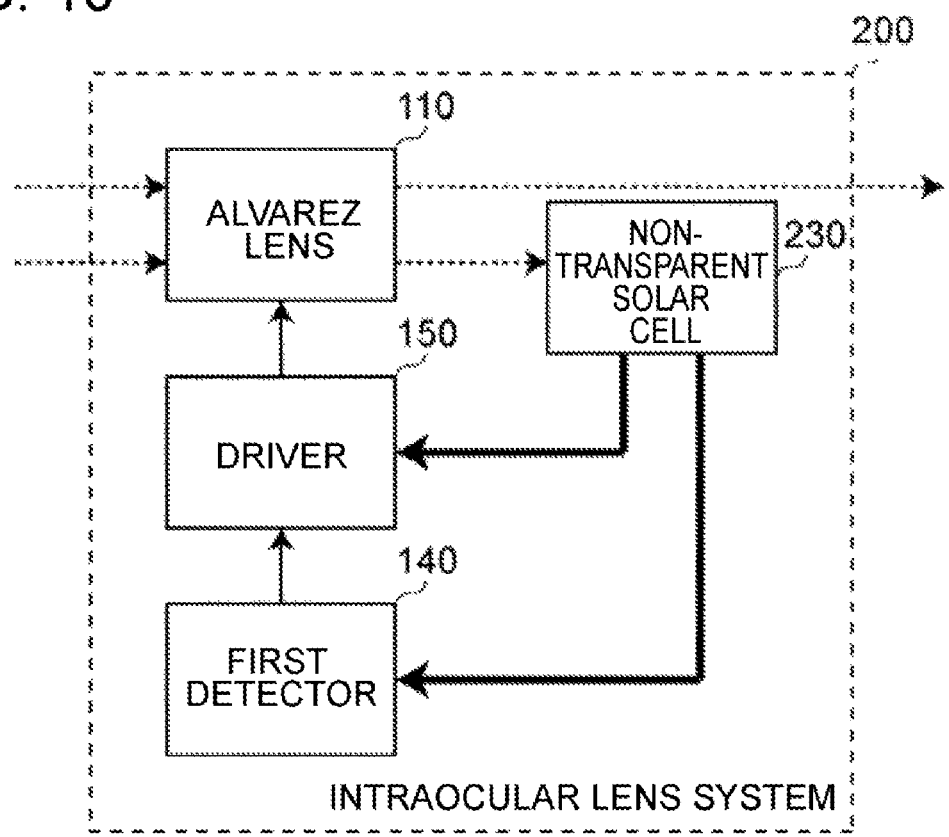
FIG. 10 is a schematic diagram illustrating an example of the configuration of an intraocular lens system according to an embodiment.

FIG. 10 is a functional block diagram illustrating an example of the configuration of an intraocular lens system according to the third embodiment. In FIG. 10, like reference numerals designate like parts as in FIG. 1, and the same description may not be repeated. In FIG. 10, the path of light is indicated by a broken arrow in distinction from the paths of others (e.g., electrical signal, etc.) each indicated by a solid line.

An intraocular lens system 200 includes the Alvarez lens 110, a non-transparent solar cell 230, the first detector 140, and the driver 150. As with the intraocular lens system 100, the intraocular lens system 200 is placed in the lens capsule. The intraocular lens system 200 is different from the intraocular lens system 100 in being provided with the non-transparent solar cell 230 in place of the transparent solar cell 130. For example, the non-transparent solar cell 230 may have a different size, shape, or the like from that of the transparent solar cell 130 to transmit part of light incident on the eye. For example, if the non-transparent solar cell 230 is smaller, it can transmit light incident on the lens capsule. For another example, if the non-transparent solar cell 230 has an opening or a cutout as described below, it can transmit light incident on the lens capsule. Besides, the non-transparent solar cell 230 may be arranged to avoid crossing over the path of light projected on the fundus center, the macula, or the like.

A power supply line connects the non-transparent solar cell 230 and the first detector 140 to supply electric power generated by the non-transparent solar cell 230. In addition, a power supply line connects the non-transparent solar cell 230 and the driver 150 to supply electric power generated by the non-transparent solar cell 230.

In this embodiment, one or more openings are formed in the non-transparent solar cell 230.

Figure 11:
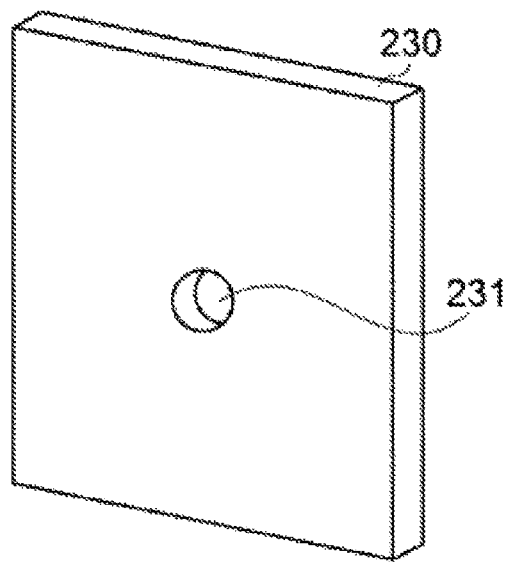
FIG. 11 is a schematic diagram illustrating an example of the configuration of an intraocular lens system according to an embodiment.
Figure 12:
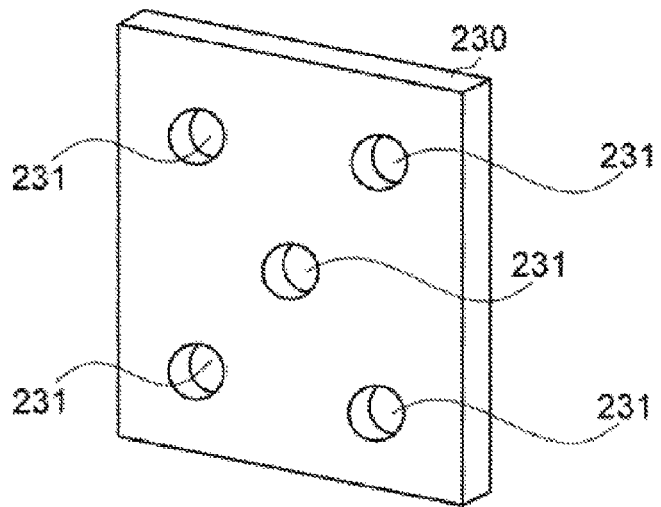
FIG. 12 is a schematic diagram illustrating an example of the configuration of an intraocular lens system according to an embodiment.

FIGS. 11 and 12 illustrate an example of the structure of the non-transparent solar cell 230 of the third embodiment. FIGS. 11 and 12 schematically illustrate a configuration in which the non-transparent solar cell 230 is placed perpendicular to the predetermined axis O of the intraocular lens system 200. As illustrated in FIG. 11, the non-transparent solar cell 230 is provided with an opening 231 that is formed in a position where light along the predetermined axis O of the intraocular lens system 200 and light around it pass through. Besides, as illustrated in FIG. 12, a plurality of openings 231 may be formed in the non-transparent solar cell 230.

As illustrated in FIG. 11 or 12, the light having transmitted through the Alvarez lens 110 passes through the opening(s) 231 formed in the non-transparent solar cell 230, and reaches the vitreous body 29.

The non-transparent solar cell 230 includes an active layer, a hole transport layer, and a hole block layer similar to those of the transparent solar cell 130, which are sealed by a non-transparent electrode, a substrate, a sealing layer, or the like. The non-transparent solar cell 230 is an example of the "converter".

In this embodiment, the non-transparent solar cell 230 may be provided with one or more openings (231) formed in a position opposite to the macula such that the light having passed through the opening(s) 231 can reach the macula where photoreceptor cells are present at high density. This enables to ensure the amount of light that reaches the macula.

This embodiment describes an example in which the non-transparent solar cell 230 is provided with one or more openings. Similarly, one or more openings may be formed in the transparent solar cell 130 of the first embodiment.

[Effects]

The intraocular lens system 200 is an example of the intraocular lens system of this embodiment. In addition to the effects of the first embodiment or the second embodiment, the intraocular lens system of this embodiment has the following advantages.

In the intraocular lens system (e.g., the intraocular lens system 200), the converter may include a non-transparent solar cell (e.g., the non-transparent solar cell 230) configured to convert the energy of light incident on the eye into electrical energy.

The non-transparent solar cell does not have the function of transmitting light incident on the eye. Light that has not entered the non-transparent solar cell reaches the retina. In the intraocular lens system, the driver is placed in the lens capsule, and can change the focal length of the lens with the electrical energy received from the converter.

In the intraocular lens system, the converter may be provided with an opening(s) (e.g., the opening(s) 231).

In the intraocular lens system, the light having passed through the opening can reach the retina. This allows an increase in the size of the light receiving surface of the converter while blocking light traveling to reach the retina as little as possible.

In the intraocular lens system, the opening may be formed in a position corresponding to the macula.

With the intraocular lens system, it is possible to increase the size of the light receiving surface of the converter as well as securing at least light that reaches the macula.

<Fourth Embodiment>

In the above embodiments, the intraocular lens system is described as being placed in the lens capsule; however, the intraocular lens system may be provided with an retinal prosthesis. In the following, an intraocular lens system according to a fourth embodiment is described focusing on differences from the first embodiment.

[Configuration]

Figure 13:
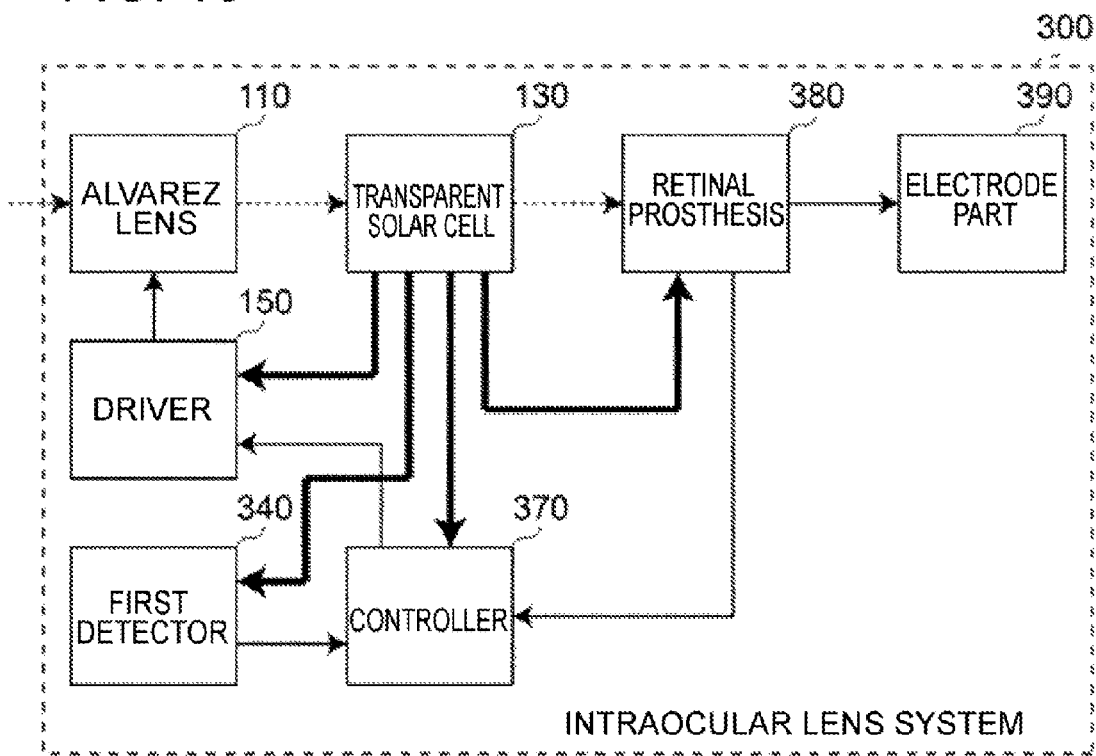
FIG. 13 is a schematic diagram illustrating an example of the configuration of an intraocular lens system according to an embodiment.

FIG. 13 is a functional block diagram illustrating an example of the configuration of an intraocular lens system according to the fourth embodiment. In FIG. 13, like reference numerals designate like parts as in FIG. 1, and the same description may not be repeated. In FIG. 13, the path of light is indicated by a broken arrow in distinction from the paths of others (e.g., electrical signal, etc.) each indicated by a solid line. An intraocular lens system 300 includes the Alvarez lens 110, the transparent solar cell 130, a first detector 340, the driver 150, a retinal prosthesis 380, an electrode part 390, and a controller 370. The intraocular lens system 300 is placed in the eye.

The Alvarez lens 110 is configured to be able to change at least the focal length. The transparent solar cell 130 is configured to transmit part of incident light therethrough and convert the energy of other part into electrical energy. The first detector 340 is configured to operate with the electrical energy received from the transparent solar cell 130 to detect the movement of the ciliary body 27 or a biological signal for moving the ciliary body. The driver 150 is configured to operate with the electrical energy received from the transparent solar cell 130 and change the focal length of the Alvarez lens 110 based on the detection result obtained by the first detector 340. The retinal prosthesis 380 is configured to operate with the electrical energy received from the transparent solar cell 130 and detect light having transmitted through the transparent solar cell 130 by a photoelectric conversion element array. The electrode part 390 is used to send an electrical signal generated by the retinal prosthesis 380 to the visual cortex of the brain. The controller 370 is configured to operate with the electrical energy received from the transparent solar cell 130 to control the driver 150. As a specific example, the controller 370 controls the driver 150 based on the detection result obtained by the first detector 340.

A power supply line connects the transparent solar cell 130 with the first detector 340 to supply the electric power generated by the transparent solar cell 130. In addition, a power supply line connects the transparent solar cell 130 with the retinal prosthesis 380 to supply the electric power generated by the transparent solar cell 130. Further, a power supply line connects the transparent solar cell 130 with the controller 370 to supply the electric power generated by the transparent solar cell 130. Besides, a biological signal line connects the first detector 340 with the controller 370 to send the detection result obtained by the first detector 340. A signal line connects the controller 370 with the driver 150 to supply a drive signal for driving the driver 150. Further, a signal line connects the retinal prosthesis 380 with the electrode part 390 to transmit the electrical signal to be sent to the visual cortex of the brain.

(First Detector)

The first detector 340 detects at least one of the acceleration of a predetermined portion of the ciliary body 27, the movement amount of a predetermined portion of the ciliary body 27, the tension of the ciliary zonule 28, and a myoelectric potential signal of the ciliary body 27, wherein the ciliary body 27 change the thickness of the crystalline lens. The first detector 340 is different from the first detector 140 in that it does not detect the pressure in the lens capsule, and that it outputs the detection result to the controller 370. Otherwise, the first detector 340 operates in the same manner as the first detector 140. The first detector 340 is an example of the "first detector".

(Retinal Prosthesis)

The retinal prosthesis 380 is provided with the photoelectric conversion element array. Each of the photoelectric conversion elements receives light having transmitted through the Alvarez lens 110 and generates an electrical signal. The retinal prosthesis 380 outputs the electrical signal to the electrode part 390. The photoelectric conversion element array includes a plurality of photoelectric conversion elements which are arranged in a matrix, for example. A retinal prosthesis having a known structure can be used as the retinal prosthesis 380. The retinal prosthesis 380 is an example of the "retinal prosthesis".

(Electrode Part)

The electrode part 390 includes a plurality of stimulating electrodes which are arranged in the shape of a matrix, for example. Each of the stimulation electrodes corresponds to one of the photoelectric conversion elements of the retinal prosthesis 380. Each of the stimulation electrodes is electrically connected to corresponding one of the photoelectric conversion elements. The stimulation electrodes are implanted to stimulate the retina 30, the optic nerve 32, and the like with the electrical signal generated by the retinal prosthesis 380. To stimulate the retina 30 by electrical signals, the stimulation electrodes are implanted such that the electrical signal is transmitted to the photoreceptor cells, the retinal ganglion cells, or the bipolar cells. The electrode part 390 is an example of the "transmitter".

(Controller)

The controller 370 includes a central processing unit (CPU) and a storage that stores a program which is executed by the CPU. The controller 370 controls the driver 150 according to the program stored in the storage. Here, the controller 370 analyzes a detection result obtained by the first detector 340 or an image detected by the retinal prosthesis 380 to control the driver 150, thereby changing the focal length of the Alvarez lens 110. The controller 370 may be implemented by an application-specific integrated circuit (ASIC) or a control circuit. The controller 370 is an example of the "controller".

[Arrangement Example]

Figure 14:
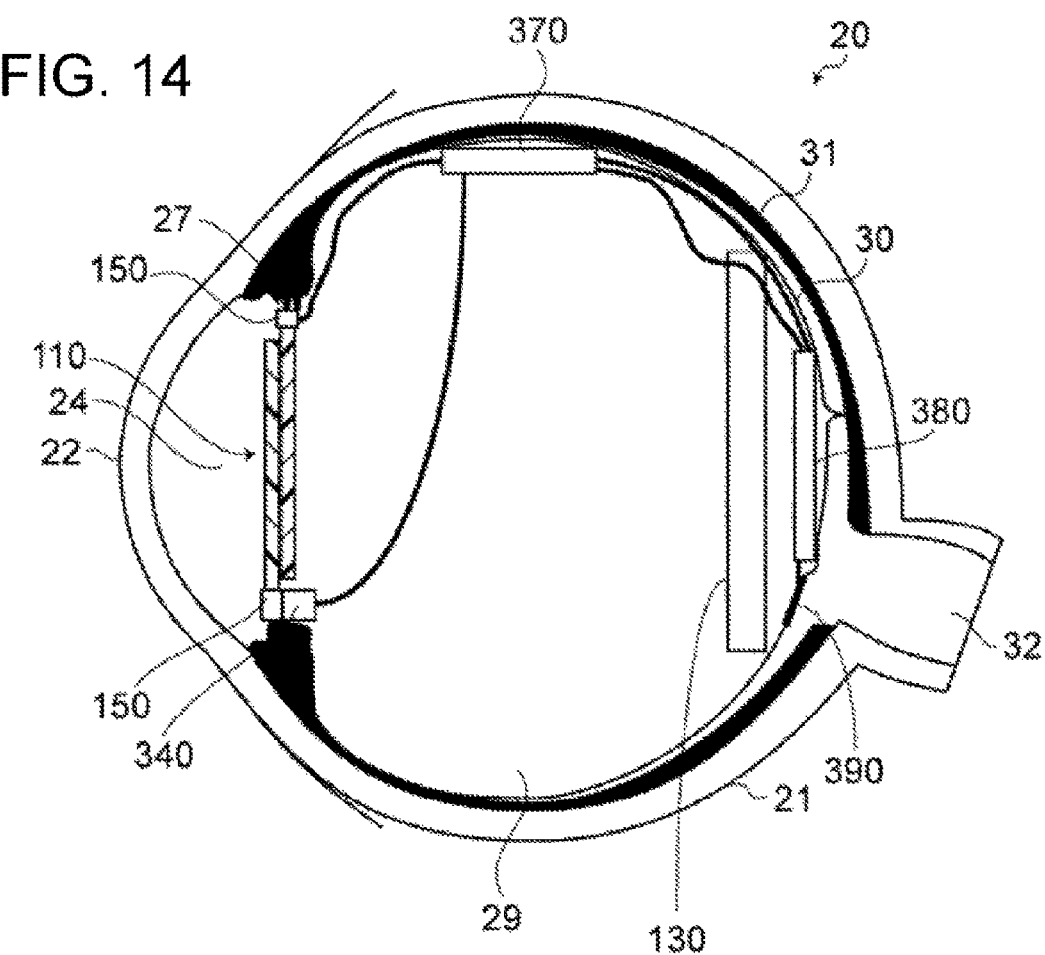
FIG. 14 is a schematic diagram illustrating an example of the configuration of an intraocular lens system according to an embodiment.

FIG. 14 is a schematic cross-sectional view of an eye in which the intraocular lens system 300 of the fourth embodiment is placed. Specifically, FIG. 14 is a cross-sectional view of the right eye as viewed from the above. Like reference numerals designate like parts as in FIG. 8 or 13, and the same description may not be repeated. For convenience of explanation, FIG. 14 may not illustrate power lines and signal lines which connect parts of the intraocular lens system 300.

The eye 20 has a substantially spherical shape and the outer is covered by the sclera 21. The light incident from the front of the eye 20 is refracted by the cornea 22, and is refracted again by the Alvarez lens 110 placed at the position of the crystalline lens.

The first detector 340 can detect the movement of the ciliary body 27 or a biological signal for moving the ciliary body 27. The detection result obtained by the first detector 340 is sent to the controller 370. The controller 370 generates a drive signal based on the detection result obtained by the first detector 340, and outputs the drive signal to the driver 150. The driver 150 drives the Alvarez lens 110 based on the drive signal received from the controller 370. Thus, the focal length of the Alvarez lens 110 is changed.

After having been refracted by the intraocular lens system 300 with the focal length changed in this manner, the light passes through the vitreous body 29 and transmits through the transparent solar cell 130. At this time, the transparent solar cell 130 converts the energy of part of the incident light into electrical energy. The electrical energy obtained by the transparent solar cell 130 is supplied to the first detector 340, the driver 150, the retinal prosthesis 380, and the controller 370.

The light having transmitted through the transparent solar cell 130 reaches the retinal prosthesis 380. The photoelectric conversion element array of the retinal prosthesis 380 receives the light and converts it into an electrical signal.

The electrical signal generated by the retinal prosthesis 380 is transmitted through the electrode part 390 to the photoreceptor cells, the retinal ganglion cells, the bipolar cells, or the optic nerve.

[Operation]

Figure 15:
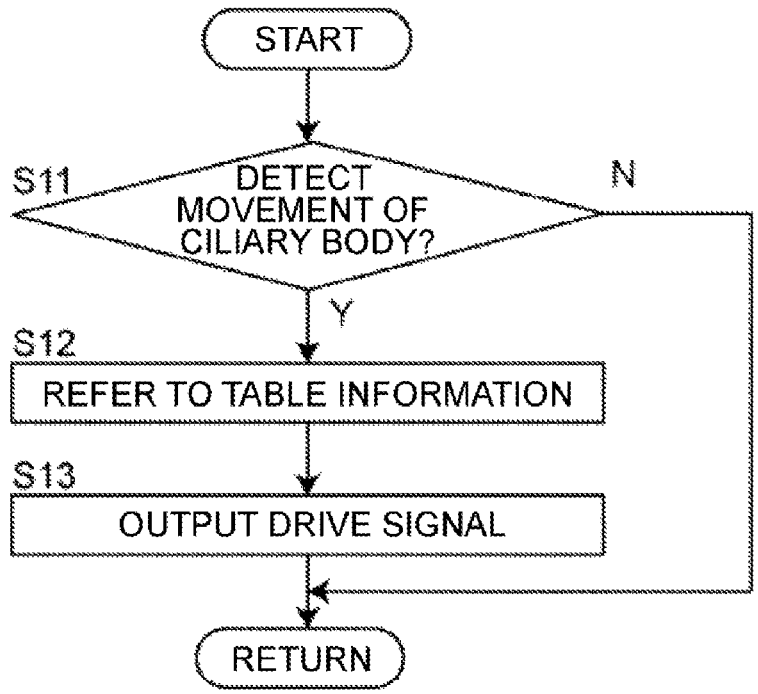
FIG. 15 is a flowchart illustrating an example of the operation of the intraocular lens system of the embodiment.

FIG. 15 is a flowchart of an example of the operation of the intraocular lens system 300 of the fourth embodiment. The storage of the controller 370 stores programs each corresponding to a step in FIG. 15. The CPU of the controller 370 reads the program from the storage, and executes it to perform a corresponding process.

(S11: Detect Movement of Ciliary Body?)

First, the controller 370 monitors whether the first detector 340 has detected the movement of the ciliary body 27 based on the detection result obtained by the first detector 340. When the first detector 340 has not detected the movement of the ciliary body 27 (step S11: N), the controller 370 continues to monitor the detection of the movement of the ciliary body 27 by the first detector 340 (Return). On the other hand, when the first detector 340 detects the movement of the ciliary body 27 (step S11: Y), the controller 370 controls the operation of the intraocular lens system 300 such that the process moves to step S12. Incidentally, in step S11, the controller 370 may monitor whether the first detector 340 has detected a biological signal for moving the ciliary body 27.

(S12: Refer to Table Information)

Table information is set in advance in which values of physical quantities detected by the first detector 340 are associated with contents (amplitudes, phases, or the like) of a drive signal. As a specific example, when the first detector 340 detects the physical quantity of any one of the acceleration of a predetermined portion of the ciliary body 27, the movement amount of a predetermined portion of the ciliary body 27, the tension of the ciliary zonule 28, and a myoelectric potential signal of the ciliary body 27, table information is set in advance in which values of this physical quantity is associated with contents of a drive signal. Besides, when the first detector 340 detects the physical quantities of two or more of the acceleration of a predetermined portion of the ciliary body 27, the movement amount of a predetermined portion of the ciliary body 27, the tension of the ciliary zonule 28, and a myoelectric potential signal of the ciliary body 27, table information is set in advance in which a combination of values of these physical quantities is associated with contents of a drive signal. The controller 370 refers to any table information as described above to generate a drive signal for changing the focal length of the Alvarez lens 110 similarly to the first detector 140 of the first embodiment. For example, the controller 370 generates a drive signal based on the content of the drive signal set in any one table information of those described above according to the detection result obtained by the first detector 340.

(S13: Output Drive Signal)

The controller 370 outputs, to the driver 150, the drive signal generated with reference to the table information in step S12. Thereafter, the controller 370 controls the operation of the intraocular lens system 300 such that the process moves to step S11 (Return).

Incidentally, in addition to the first detector 340, there may be provided a means for detecting the eye movement. In this case, based on the detection results obtained by the first detector 340 and the means, the controller 370 cancels information on the eye movement from the detection result obtained by the first detector 340 to thereby extract substantial information required to change the thickness of the crystalline lens.

Further, in this embodiment, as in the second embodiment, the transparent solar cell 130 may be placed on the cornea side, and the Alvarez lens 110 may be placed on the fundus side. In this case, the Alvarez lens 110 is located between the transparent solar cell 130 and the retinal prosthesis 380.

[Effects]

The intraocular lens system 300 is an example of the intraocular lens system of this embodiment. Described below are the effects of the intraocular lens system of this embodiment.

The intraocular lens system includes a lens (e.g., the Alvarez lens 110), a converter (e.g., the transparent solar cell 130), a driver (e.g., the driver 150), a retinal prosthesis (e.g., the retinal prosthesis 380), and a transmitter (e.g., the electrode part 390).

The lens is placed in the eye, and configured to allow changes of the focal length. The converter is placed in the eye, and configured to transmit part of light incident on the eye therethrough and convert the energy of other part of the light into electrical energy. Here, "other part of the light" may include the entire part of the light incident on the eye excluding the part of the light that transmits through the converter. The driver is placed in the eye, and configured to operate with the electrical energy received from the converter to change the focal length of the lens. The retinal prosthesis is placed in the eye, and includes a photoelectric conversion element array configured to operate with the electrical energy received from the converter to detect the light having transmitted through the converter to generate an electrical signal. The transmitter is used to send the electrical signal generated by the retinal prosthesis to the visual cortex of the brain.

In the intraocular lens system, the converter converts the energy of light incident on the eye into electrical energy. The driver receives the electrical energy from the converter to drive the lens. With this, the lens can be placed in the eye in a conventional manner. Further, the focal length of the lens can be changed appropriately by using the energy of light incident on the eye.

In addition, the intraocular lens system may include a first detector (e.g., the first detector 340) configured to be placed in the eye, and detect the movement of the ciliary body or a biological signal for moving the ciliary body. The driver can change the focal length of the lens based on the detection result obtained by the first detector.

With the intraocular lens system thus configured, since the first detector detects the movement of the ciliary body or a biological signal for moving the ciliary body, the driver can change the focal length of the lens by amplifying the movement of the ciliary body. Thus, even if the movement of the ciliary body is insufficient, the focal length of the lens can be changed appropriately by amplifying the movement of the ciliary body.

In the intraocular lens system, the first detector may be configured to detect at least one of the acceleration of a predetermined portion of the ciliary body, the movement amount of a predetermined portion of the ciliary body, the tension of the ciliary zonule, and a myoelectric potential signal of a predetermined portion of the ciliary body.

The movement of the ciliary body leads to a change in the acceleration of the predetermined portion of the ciliary body, the movement amount of the predetermined portion of the ciliary body, the tension of the ciliary zonule, or the myoelectric potential signal of the predetermined portion of the ciliary body. Therefore, the first detector is provided to detect such physical quantities. Thereby, the movement of the ciliary body can be detected with high accuracy. Thus, the lens can be controlled to be driven with high accuracy according to the movement of the ciliary body.

In addition, the intraocular lens system may include a controller (e.g., the controller 370). In this case, the controller is configured to operate with the electrical energy received from the converter and control the driver.

With the intraocular lens system provided with the controller that operates with the electrical energy obtained by the converter, the driver can be controlled more finely. Thus, the focal length of the lens can be changed more appropriately.

In the intraocular lens system, the converter may include a transparent solar cell configured to transmit part of light incident on the eye and convert the energy of other part into electrical energy.

The transparent solar cell transmits light incident on the eye. The light having transmitted through the transparent solar cell reaches the retinal prosthesis. With this, it becomes possible to secure the size of the light receiving surface of the transparent solar cell without blocking the light to reach the retinal prosthesis. Thus, it is possible to generate more electrical power without blocking the light to reach the retinal prosthesis. Further, it is possible to suppress a decrease in the light absorption efficiency of the retinal prosthesis. Thereby, more information can be transmitted to the optic nerve.

In the intraocular lens system, the lens may include an Alvarez lens.

With the intraocular lens system thus configured, the focal length can be changed with the use of the Alvarez lens by using electrical power generated in the eye.

<Fifth Embodiment>

According to a fifth embodiment, the Alvarez lens 110 is driven based on an image detected by the retinal prosthesis 380. In the following, an intraocular lens system according to the fifth embodiment is described focusing on differences from the fourth embodiment.

[Configuration]

The intraocular lens system of the fifth embodiment has basically the same configuration as the intraocular lens system 300 of the fourth embodiment. The intraocular lens system of the fifth embodiment is described below with reference to FIGS. 13 and 14.

[Operation]

Figure 16:
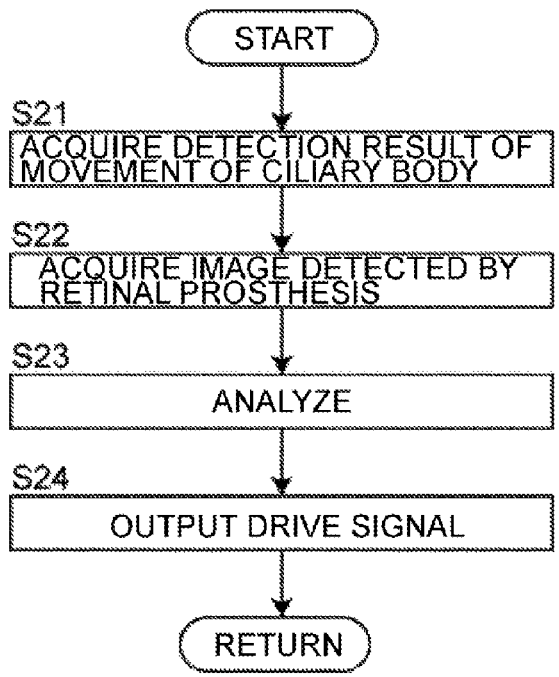
FIG. 16 is a flowchart illustrating an example of the operation of the intraocular lens system of the embodiment.

FIG. 16 is a flowchart of an example of the operation of the intraocular lens system of the fifth embodiment. The storage of the controller 370 stores programs each corresponding to a step in FIG. 16. The CPU of the controller 370 reads the program from the storage, and executes it to perform a corresponding process.

(S21: Acquire Detection Result of Movement of Ciliary Body)

First, the controller 370 acquires a detection result of the movement of the ciliary body 27 obtained by the first detector 340. The detection result includes the detection result of the physical quantity of at least one of the acceleration of a predetermined portion of the ciliary body 27, the movement amount of a predetermined portion of the ciliary body 27, the tension of the ciliary zonule 28, and a myoelectric potential signal of the ciliary body 27.

(S22: Acquire Image Detected by Retinal Prosthesis)

Next, the controller 370 acquires an image detected by the retinal prosthesis 380. As a specific example, the controller 370 acquires an electrical signal generated by each of the photoelectric conversion elements in the retinal prosthesis 380.

(S23: Analyze)

Next, the controller 370 analyzes at least one of the detection result obtained in step S21 and the image acquired in step S22. The controller 370 generates a drive signal to drive the driver 150 based on the result of the analysis.

For example, the controller 370 generates a drive signal corresponding to the detection result obtained by the first detector 340. As a specific example, the controller 370 determines whether the movement of the ciliary body 27 is a movement for thickening the crystalline lens or a movement for thinning the crystalline lens based on the detection result obtained by the first detector 340. The controller 370 generates a drive signal based on the result of the determination. Upon detection of the movement of the ciliary body for thickening the crystalline lens, the controller 370 generates a drive signal to reduce the current focal length of the Alvarez lens 110. Upon detection of the movement of the ciliary body for thinning the crystalline lens, the controller 370 generates a drive signal to increase the current focal length of the Alvarez lens 110. At this time, the controller 370 may generate the drive signal so as to amplify the movement of the ciliary body 27. For example, when the first detector 340 detects a very small amount of movement of the ciliary body 27, the controller 370 multiplies the small amount of movement by an amplification factor corresponding to the amount of the movement to generate the drive signal. The focal length of the Alvarez lens 110 is changed based on the drive signal thus generated. The amplification factor corresponding to the amount of the movement can be changed afterwards. The drive signal is a signal corresponding to the amount and direction of the change of the focal length.

For example, the controller 370 generates a drive signal corresponding to the sharpness of the image obtained by the retinal prosthesis 380. As a specific example of this case, the controller 370 detects lines in an image obtained by the retinal prosthesis 380. The controller 370 generates a drive signal to change the focal length in stages by a first step in a direction in which the harmonic components of the boundary of the lines detected are emphasized. The controller 370 also detects the edge of the image obtained by the retinal prosthesis 380. The controller 370 generates a drive signal to change the focal length in stages by a second step in a direction in which the harmonic components of the edge detected are emphasized. Further, the controller 370 detects the contrast of the image obtained by the retinal prosthesis 380. The controller 370 generates a drive signal to change the focal length in stages by a third step in a direction in which the contrast of the image is the maximum.

For another example, the controller 370 may generate a drive signal based on the detection result obtained by the first detector 340 and the image obtained by the retinal prosthesis 380. As a specific example of this case, when the movement of the ciliary body 27 is a movement for thickening the crystalline lens, the controller 370 generates a drive signal to reduce the current focal length of the Alvarez lens 110 in stages by a fourth step in a direction in which the harmonic components of the boundary of the lines, the edge in the image, or the like is emphasized. Each of the first to the fourth steps can be changed afterwards.

(S24: Output Drive Signal)

The controller 370 outputs the drive signal generated in step S23 to the driver 150. Thereafter, the controller 370 controls the operation of the intraocular lens system such that the process moves to step S21 (Return).

[Effects]

The above intraocular lens system is an example of the intraocular lens system of this embodiment. In addition to the effects of the fourth embodiment, the intraocular lens system of this embodiment has the following advantages.

In the intraocular lens system, the controller may control the driver based on an electrical signal generated by the retinal prosthesis.

The electrical signal generated by the retinal prosthesis corresponds to an image detected by the retinal prosthesis. The controller may control the driver based on, for example, the sharpness, information on the edge, the contrast, or the like of the image obtained by the retinal prosthesis. With the intraocular lens system thus configured, the focal length of the lens can be changed based on the electrical signal generated by the retinal prosthesis. Thus, even if it is not sufficient just to detect the movement of the ciliary body or a biological signal for moving the ciliary body, the focal length of the lens can be changed more appropriately.

<Sixth Embodiment>

In the intraocular lens system of the above embodiments, the focal length of the Alvarez lens 110 may be changed according to the orientation of the eye (viewing direction, eye axis direction, visual axis direction, or the like). An intraocular lens system of a sixth embodiment has basically the same configuration as that of the fourth embodiment except the presence of a second detector to change the focal length of the Alvarez lens 110 according to the orientation of the eye. In the following, the intraocular lens system of the sixth embodiment is described focusing on differences from the fourth embodiment.

[Configuration]

Figure 17:
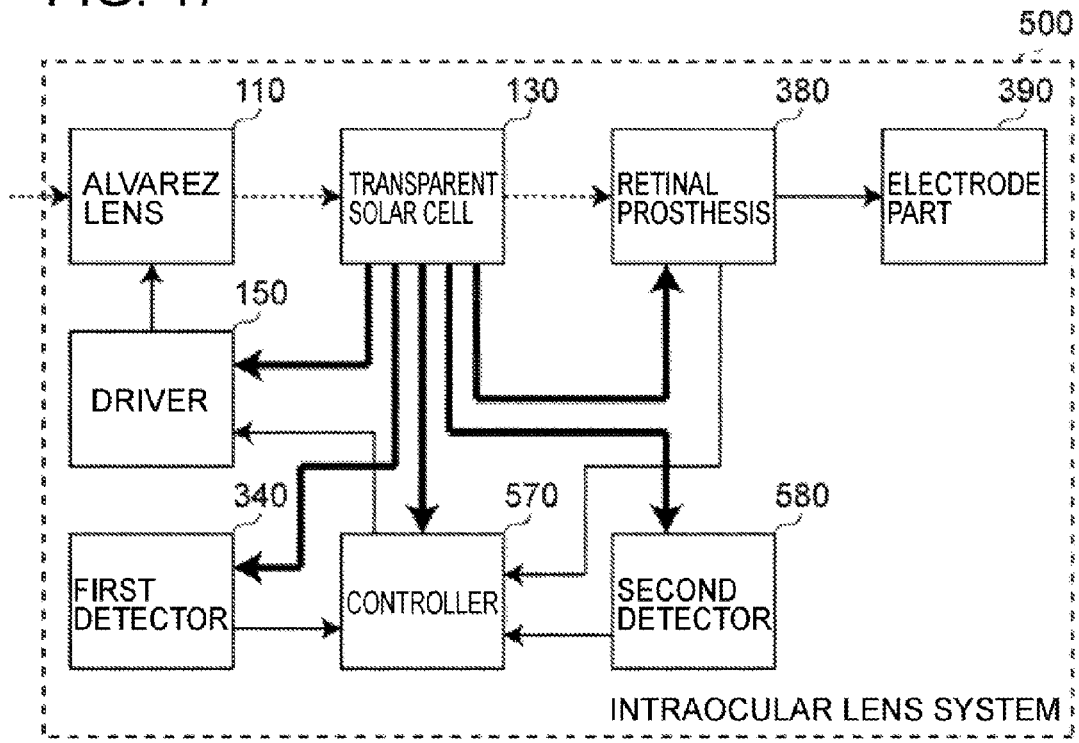
FIG. 17 is a schematic diagram illustrating an example of the configuration of an intraocular lens system according to an embodiment.

FIG. 17 is a functional block diagram illustrating an example of the configuration of an intraocular lens system according to the sixth embodiment. In FIG. 17, like reference numerals designate like parts as in FIG. 13, and the same description may not be repeated. In FIG. 17, the path of light is indicated by a broken arrow in distinction from the paths of others (e.g., electrical signal, etc.) each indicated by a solid line. An intraocular lens system 500 includes the Alvarez lens 110, the transparent solar cell 130, the first detector 340, the driver 150, the retinal prosthesis 380, the electrode part 390, a controller 570, and a second detector 580. The intraocular lens system 500 is placed in the eye.

The intraocular lens system 500 of the sixth embodiment is different from the intraocular lens system 300 of the fourth embodiment in the presence of the second detector 580 and in the provision of the controller 570 in place of the controller 370.

A power supply line connects the transparent solar cell 130 with the controller 570 to supply the electric power generated by the transparent solar cell 130. In addition, a power supply line connects the transparent solar cell 130 with the second detector 580 to supply the electric power generated by the transparent solar cell 130. Besides, a signal line connects the controller 570 with the driver 150 to supply a drive signal for driving the driver 150. Further, a signal line connects the controller 570 with the second detector 580 to send the detection result obtained by the second detector 580.

(Controller)

The controller 570 has basically the same configuration as the controller 370. The controller 570 is capable of generating a drive signal for driving the driver 150 based on the detection result obtained by the second detector 580 in addition to the detection result obtained by the first detector 340. The controller 570 is an example of the "controller".

(Second Detector)

The second detector 580 operates with the electrical energy obtained by the transparent solar cell 130, and detects the orientation of the eye where the intraocular lens system 500 is located. The second detector 580 includes a tilt sensor or the like attached to a predetermined portion of the eye (inside of the eye (the retina, etc.)) to detect the orientation of the eye. The tilt sensor is configured to detect an angle of inclination corresponding to the change amount of electrostatic capacitance when it is inclined, for example, with respect to the vertical direction using the electrostatic capacitance when it is held horizontally as a reference. The tilt sensor can also detect inclination in other directions such as left and right directions with a similar configuration. The orientation of the eye is specified by, for example, the detection result obtained by the tilt sensor that detects a vertical tilt. In addition, the orientation of the eye may be specified by detection results obtained by a plurality of tilt sensors each detecting an inclination in one of the two axial directions or three axial directions, which are perpendicular to one another and include the vertical direction. The detection result obtained by the second detector 580 is sent to the controller 570. The second detector 580 is an example of the "second detector".

[Arrangement Example]

Figure 18:
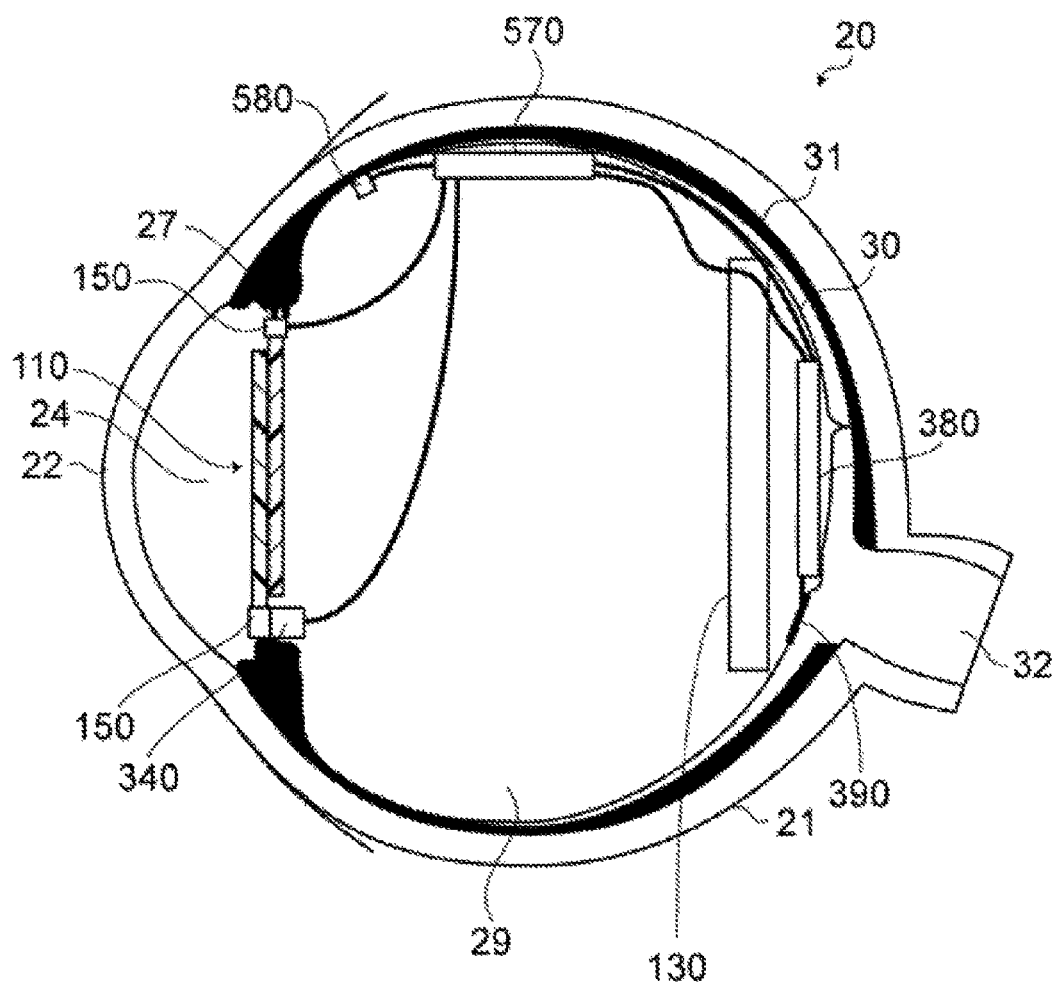
FIG. 18 is a schematic diagram illustrating an example of the configuration of an intraocular lens system according to an embodiment.

FIG. 18 is a schematic cross-sectional view of an eye in which the intraocular lens system 500 of the sixth embodiment is placed. FIG. 18 is a cross sectional view of the right eye as viewed from the above. Like reference numerals designate like parts as in FIGS. 14 and 17, and the same description may not be repeated. For convenience of explanation, FIG. 18 may not illustrate power lines and signal lines which connect parts of the intraocular lens system 500.

The eye 20 has a substantially spherical shape and the outer is covered by the sclera 21. The light incident from the front of the eye 20 is refracted by the cornea 22, and is refracted again by the Alvarez lens 110 placed at the position of the crystalline lens.

The controller 570 generates a drive signal based on at least one of the detection result obtained by the first detector 340 and the detection result obtained by the second detector 580, and outputs the drive signal to the driver 150. The driver 150 drives the Alvarez lens 110 based on the drive signal received from the controller 570. Thus, the focal length of the Alvarez lens 110 is changed.

After having been refracted by the intraocular lens system 500 with the focal length changed in this manner, the light passes through the vitreous body 29 and transmits through the transparent solar cell 130. At this time, the transparent solar cell 130 converts the energy of part of the incident light into electrical energy. The electrical energy generated by the transparent solar cell 130 is supplied to the first detector 340, the driver 150, the retinal prosthesis 380, the controller 570, and the second detector 580.

The light having transmitted through the transparent solar cell 130 reaches the retinal prosthesis 380. The photoelectric conversion element array of the retinal prosthesis 380 converts the light into an electrical signal. The electrical signal generated by the retinal prosthesis 380 is transmitted through the electrode part 390 to the photoreceptor cells, the retinal ganglion cells, the bipolar cells, or the optic nerve.

[Operation]

Figure 19:
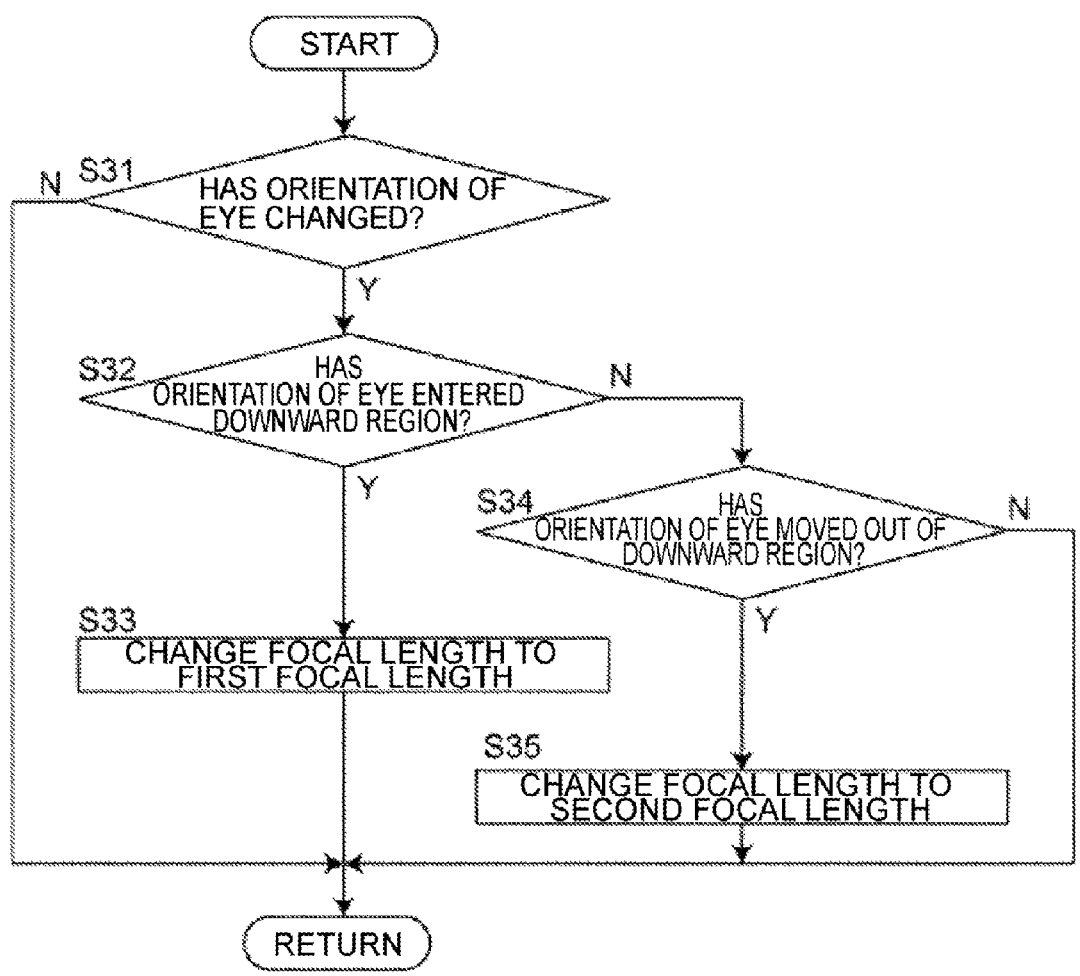
FIG. 19 is a flowchart illustrating an example of the operation of the intraocular lens system of the embodiment.

FIG. 19 is a flowchart of an example of the operation of the intraocular lens system 500 of the sixth embodiment. The storage of the controller 570 stores programs each corresponding to a step in FIG. 19. The CPU of the controller 570 reads the program from the storage, and executes it to perform a corresponding process.

(S31: Has Orientation of Eye Changed?)

First, the controller 570 monitors whether the orientation of the eye 20 has changed based on the detection result obtained by the second detector 580. Having detected no change in the orientation of the eye based on the detection result obtained by the second detector 580 (step S31: N), the controller 570 continues to monitor the detection of a change in the orientation of the eye 20 by the second detector 580 (Return). On the other hand, when the second detector 580 has detected a change in the orientation of the eye 20 (step S31: Y), the controller 370 controls the operation of the intraocular lens system 500 such that the process moves to step S32.

(S32: has Orientation of Eye Entered Downward Region?)

When the second detector 580 has detected a change in the orientation of the eye 20, the controller 570 determines whether the orientation of the eye 20 has entered from the front direction into a downward region located below based on the detection result obtained by the second detector 580. Having determined that the orientation of the eye 20 has entered the downward region (step S32: Y), the controller 570 controls the operation of the intraocular lens system 500 such that the process moves to step S33. On the other hand, having determined that the orientation of the eye 20 has not entered the downward region (step S32: N), the controller 570 controls the operation of the intraocular lens system 500 such that the process moves to step S34.

(S33: Change Focal Length to First Focal Length)

Having determined that the orientation of the eye 20 has changed to downward based on the detection result obtained by the second detector 580, the controller 570 generates a drive signal to set the focal length of the Alvarez lens 110 to a first focal length that is shorter than the current focal length, and outputs the drive signal to the driver 150.

(S34: has Orientation of Eye Moved Out of Downward Region?)

When the second detector 580 has not detected that the orientation of the eye 20 has entered the downward region, the controller 570 determines whether the orientation of the eye 20 has moved out of the downward region based on the detection result obtained by the second detector 580. Having determined that the orientation of the eye 20 has moved out of the downward region (step S34: Y), the controller 570 controls the operation of the intraocular lens system 500 such that the process moves to step S35. On the other hand, having determined that the orientation of the eye 20 has not moved out of the downward region (step S34: N), the controller 570 controls the operation of the intraocular lens system 500 such that the process moves to step S31 (Return).

(S35: Change Focal Length to Second Focal Length)

Having determined that the orientation of the eye 20 has moved out of the downward region based on the detection result obtained by the second detector 580, the controller 570 generates a drive signal to set the focal length of the Alvarez lens 110 to a second focal length that is longer than the current focal length. The second focal length is longer than the first focal length. The controller 570 outputs the drive signal to the driver 150.

After step S33 or step S35, the controller 570 controls the operation of the intraocular lens system 500 such that the process loops back to step S31 (Return).

As described above, when the second detector 580 has detected that the eye 20 is directed downward, the controller 570 can change the focal length of the Alvarez lens 110 to the first focal length that is shorter than the current focal length. Otherwise, the controller 570 can change the focal length of the Alvarez lens 110 to the second focal that is longer than the current focal length. Here, the second focal length is longer than the first focal length.

Although this embodiment describes an example in which the second detector 580 detects the orientation of the eye, and the focal length of the Alvarez lens 110 is changed according to the orientation of the eye, this is not a limitation.

The second detector 580 may detect convergence eye movement (convergence). The convergence eye movement is the movement of the left and right eyes turning inward (towards the nose side) to see a nearby object. In this case, the controller 570 changes the focal length of the Alvarez lens 110 based on the detection result obtained by the second detector 580. As a specific example, when the second detector 580 has detected that the eye 20 is in a first convergence state, the controller 570 changes the focal length of the Alvarez lens 110 to a third focal length. The first convergence state is a state where the eyes are directed more inside than a predetermined direction (e.g., the front direction). Incidentally, in addition to the second detector 580, there may be provided a means for detecting the convergence eye movement of the other eye. In this case, the controller 570 can determine, for example, whether the eyes have moved to simply change the viewing direction to the diagonal direction (that is, the left and right eyes both turn in the same direction) or the convergence eye movement has occurred (that is, the left and right eyes both turn inside) based on the detection result obtained by the second detector 580 and the detection result obtained by the means.

Further, although this embodiment describes an example in which the orientation of the eye is detected by the second detector 580, which is added to the configuration of the fourth embodiment, this is not a limitation. The controller 370 of the fourth embodiment may be configured to analyze, for example, an image detected by the retinal prosthesis 380 (an electrical signal generated by the retinal prosthesis) to determine the orientation of the eye. As a specific example, the controller 370 obtains a change (direction, amount) in the orientation of the eye based on the change of an image in a predetermined area (e.g., central area including the center) of the image detected by the retinal prosthesis 380. In addition, the controller 370 obtains a change in the orientation of the eye based on a change in the position of an image of interest in the image detected by the retinal prosthesis 380. In this case, having determined that the eyes are directed downward based on the image detected by the retinal prosthesis 380 (an electrical signal generated by the retinal prosthesis), the controller 370 changes the focal length of the Alvarez lens 110 to a fifth focal length that is shorter than the current focal length.

[Effects]

The intraocular lens system 500 is an example of the intraocular lens system of this embodiment. In addition to the effects of the fourth embodiment or the fifth embodiment, the intraocular lens system of this embodiment has the following advantages.

The intraocular lens system (e.g., the intraocular lens system 500) may include a second detector (e.g., the second detector 580) configured to be placed in the eye to detect the orientation of the eye. In this case, the second detector operates with the electrical energy received from the converter. The controller controls the driver based on the detection result obtained by the second detector.

With the intraocular lens system thus configured, the orientation of the eye is detected in the eye so that the focal length of the lens can be changed depending on the orientation of the eye detected. Thus, when it can be specified whether to increase or reduce the focal length according to the orientation of the eye, the focal length of the lens can be changed based on the orientation of the eye detected.

In the intraocular lens system, when the second detector has detected that the eye is directed downward, the controller may change the focal length of the lens to a first focal length. Otherwise, the controller may change the focal length of the lens to a second focal length that is longer than the first focal length.

To see a nearby object (e.g., when reading a book, etc.), the eyes are generally pointed downward. Therefore, when the second detector has detected that the eyes are directed downward, the controller controls the lens to have the first focal length. Otherwise, the controller controls the lens to have the second focal length that is longer than the first focal length. Thus, the focal length of the lens can be changed appropriately according to the natural movement of the eyes.

In the intraocular lens system, the second detector may detect at least one of the acceleration of a predetermined portion of the eye and the convergence eye movement.

To see a nearby object, there is a change in the acceleration of a predetermined portion of the eye, or the convergence eye movement occurs. Therefore, the second detector is provided to detect such a movement. Thereby, a movement to see a nearby object can be detected with high accuracy. Thus, the lens can be controlled to be driven with high accuracy according to the movement of the eye.

<Seventh Embodiment>

In the fourth embodiment, the converter for converting light energy into electrical energy is described as being transmissive by way of example. However, the converter may be non-transmissive as in the third embodiment. In the following, an intraocular lens system according to a seventh embodiment is described focusing on differences from the fourth embodiment.

[Configuration]

Figure 20:
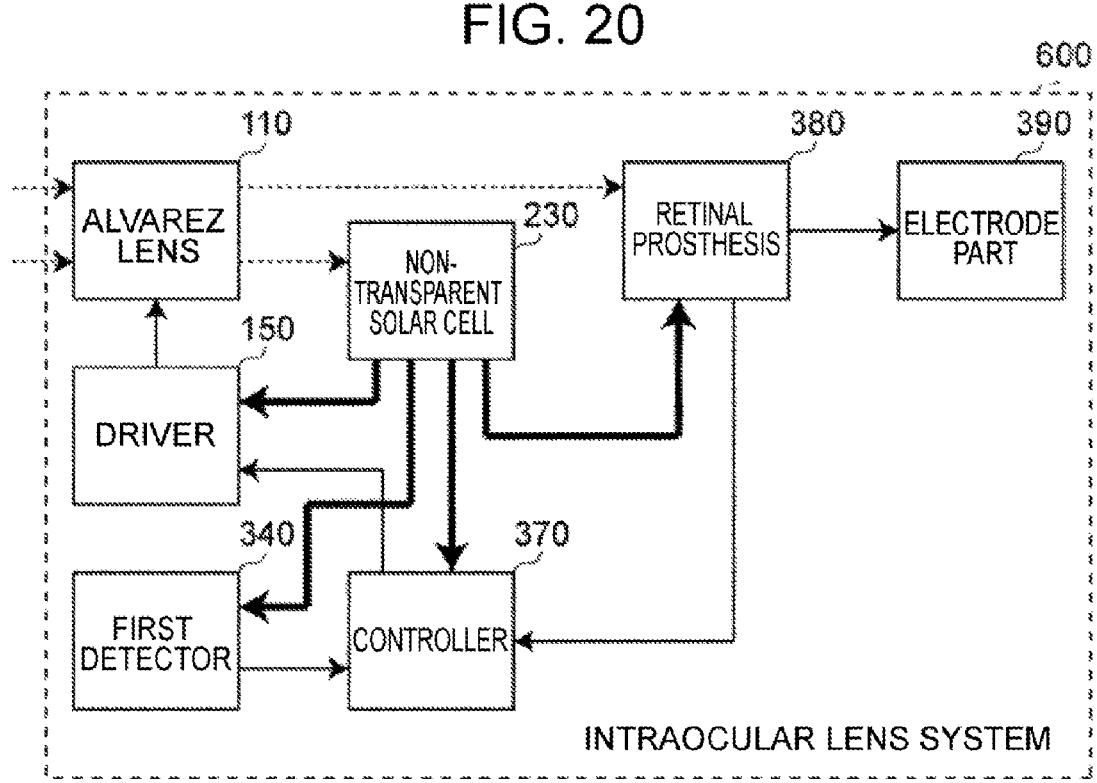
FIG. 20 is a schematic diagram illustrating an example of the configuration of an intraocular lens system according to an embodiment.

FIG. 20 is a functional block diagram illustrating an example of the configuration of an intraocular lens system according the seventh embodiment. In FIG. 20, like reference numerals designate like parts as in FIG. 10 or 13, and the same description may not be repeated. In FIG. 20, the path of light is indicated by a broken arrow in distinction from the paths of others (e.g., electrical signal, etc.) each indicated by a solid line.

An intraocular lens system 600 includes the Alvarez lens 110, the non-transparent solar cell 230, the first detector 340, the driver 150, the retinal prosthesis 380, the electrode part 390, and the controller 370. As with the intraocular lens system 300, the intraocular lens system 600 is placed in the eye. The intraocular lens system 600 is different from the intraocular lens system 300 in being provided with the non-transparent solar cell 230 in place of the transparent solar cell 130. As illustrated in FIG. 11 or 12, the non-transparent solar cell 230 is provided with one or more openings (the opening(s) 231). The light having transmitted through the Alvarez lens 110 passes through the opening(s) 231 formed in the non-transparent solar cell 230, and reaches the vitreous body 29.

In the intraocular lens system 600, a power supply line connects the non-transparent solar cell 230 with the first detector 340 to supply electric power generated by the non-transparent solar cell 230. A power supply line connects the non-transparent solar cell 230 with the driver 150 to supply electric power generated by the non-transparent solar cell 230. In addition, a power supply line connects the non-transparent solar cell 230 with the retinal prosthesis 380 to supply electric power generated by the non-transparent solar cell 230. Further, a power supply line connects the non-transparent solar cell 230 and the controller 370 to supply electric power generated by the non-transparent solar cell 230.

In this embodiment, the photoelectric conversion element array of the retinal prosthesis 380 receives the light having passed through the opening(s) 231 formed in the non-transparent solar cell 230, and generates an electrical signal. The opening 231 formed in the non-transparent solar cell 230 may be located in a position opposite to the macula in the retinal prosthesis 380.

In this embodiment, although the non-transparent solar cell 230 is described as being provided with an opening, the non-transparent solar cell 230 may be provided with a cutout. Further, in this embodiment, while the non-transparent solar cell 230 is described as being provided with one or more openings, the transparent solar cell 130 of the fourth embodiment may be provided with one or more openings or cutouts.

[Effects]

The intraocular lens system 600 is an example of the intraocular lens system of this embodiment. In addition to the effects of the fourth embodiment, the intraocular lens system of this embodiment has the following advantages.

In the intraocular lens system (e.g., the intraocular lens system 600), the converter may include a non-transparent solar cell (e.g., the non-transparent solar cell 230) configured to convert the energy of light incident on the eye into electrical energy.

The non-transparent solar cell does not have the function of transmitting light incident on the eye. Light that has not entered the non-transparent solar cell reaches the retinal prosthesis. In the intraocular lens system, the driver is placed in the eye and can change the focal length of the lens with the electrical energy received from the converter.

In the intraocular lens system, the converter may be provided with an opening (e.g., the opening(s) 231).

In the intraocular lens system thus configured, the light having passed through the opening can reach the retinal prosthesis. This allows an increase in the size of the light receiving surface of the converter while blocking light traveling to reach the retinal prosthesis as little as possible.

In the intraocular lens system, the opening may be formed in a position corresponding to the macula in the retinal prosthesis.

With the intraocular lens system thus configured, it is possible to sufficiently secure both of the size of the light receiving surface of the converter and the size of the retinal prosthesis.

In the intraocular lens system, the photoelectric conversion element array may be configured to receive the light having passed through the opening and generate the electrical signal.

With the intraocular lens system thus configured, it is possible to secure the size of the light receiving surface of the converter to generate more electrical power. Further, the size of the retinal prosthesis can also be secured. Thus, more information can be transmitted to the visual cortex.

<Eighth Embodiment>

In the seventh embodiment, in the opening formed in the non-transparent solar cell 230, a lens for adjusting a light flux that reaches the macula may be provided. With such a configuration, the size of the opening can be adjusted.

Therefore, it is possible to secure a large area of the light receiving portion of the non-transparent solar cell 230, for example, resulting in an increase in electrical power to be generated. Besides, if the Alvarez lens 110 is located in front of the non-transparent solar cell 230, it is possible to increase the area of the retinal prosthesis 380 that is placed behind the non-transparent solar cell 230. Accordingly, the size of an image detected by the retinal prosthesis 380 can also be increased. As a result, it is possible to improve the accuracy of control based on the image detected in the retinal prosthesis 380.

Incidentally, the transparent solar cell 130 may also include a lens that is provided in the opening for adjusting a light flux that reaches the macular. In this case also, the same effects as above can be achieved.

[Effects]

The intraocular lens system described in the eighth embodiment is an example of the intraocular lens system of the embodiment. In addition to the effects of the seventh embodiment, the intraocular lens system of this embodiment has the following advantages.

In the intraocular lens system, a lens for adjusting a light flux that reaches the macula may be provided in the opening.

With the intraocular lens system thus configured, it is possible to secure a large area of the light receiving portion of the non-transparent solar cell. Thus, more electrical power can be generated. Further, the size of the retinal prosthesis can be increased. Accordingly, the size of an image detected by the retinal prosthesis can also be increased. As a result, it is possible to improve the accuracy of control based on the image detected in the retinal prosthesis.

(First Modification)

In the above embodiments of the intraocular lens system, examples are described in which the spherical diopter power is changed by the Alvarez lens. For another example, the astigmatic power may be changed by the Alvarez lens. For example, in FIG. 2, by relatively moving the optical elements 111 and 112 in the x direction (horizontal direction) within the xy plane perpendicular to the axis O, the astigmatic power (refractive power) obtained by optically combining the optical elements 111 and 112 can be continuously changed. In FIG. 2, the optical element 111 is moved to the left (−x direction), while the optical element 112 is moved to the right (+x direction).

Besides, a variable cross cylinder lens may be placed on the incident side of the Alvarez lens 110 to change the astigmatic power. The variable cross cylinder lens is formed of a pair of cylindrical lenses. In this case, by relatively rotating the cylindrical lenses, the astigmatic power obtained by optically combining the cylindrical lenses continuously changes. For example, a known ultrasonic linear motor drives one of the cylindrical lenses to rotate in the positive rotation direction, and drives the other of them to rotate in the negative rotation direction.

Further, a prism, which changes the orientation of optical elements, the direction of a light ray, or the like, may be placed on the incident side or emission side of the Alvarez lens 110 to change an arbitrary optical property such as the transmission wavelength, the transmittance, the magnification, or the like.

(Second Modification)

In the intraocular lens system of the above embodiments or the first modification, an example is described in which an Alvarez lens is used as the variable focus lens; however, this is not a limitation.

Figure 21:
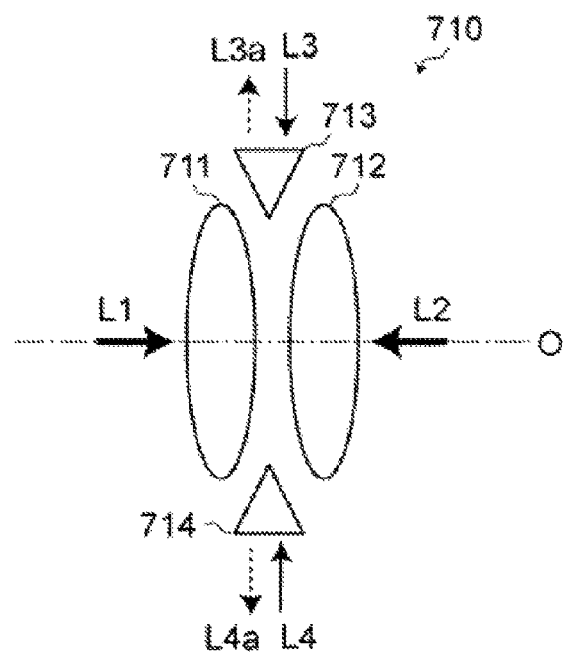
FIG. 21 is a schematic diagram illustrating an example of the configuration of an intraocular lens system according to an embodiment.

FIG. 21 is a cross-sectional view illustrating an example of the configuration of a lens according to a second modification. FIG. 21 is a schematic vertical cross-sectional view, passing through the axis O, of the lens of the second modification as viewed from the side.

A lens 710 of the second modification includes a pair of optical elements 711 and 712, and a pair of wedge members (spacers) 713 and 714. The optical elements 711 and 712 are placed such that the predetermined axis O of the lens 710 matches the optical axis. The optical element 711 is biased (energized) by a first biasing means (not illustrated) in a first direction L1 along the axis O. The optical element 712 is biased by a second biasing means (not illustrated) in a second direction L2 opposite to the first direction L1 along the axis O. The wedge members 713 and 714 are configured to be movable in a third direction L3 and a fourth direction L4 perpendicular to the first direction L1 and the second direction L2 such that a space between the optical elements 711 and 712 can be changed. Upon increasing the space between the optical elements 711 and 712, the wedge members 713 and 714 are brought close to each other. As a specific example, upon increasing the space between the optical elements 711 and 712, the wedge member 713 is moved in the third direction L3 by the driver 150 based on a drive signal, while the wedge member 714 is moved in the fourth direction L4 by the driver 150 based on a drive signal. Upon reducing the space between the optical elements 711 and 712, the wedge members 713 and 714 are separated from each other. As a specific example, upon reducing the space between the optical elements 711 and 712, the wedge member 713 is moved in a direction L3a opposite to the third direction L3 by the driver 150 based on a drive signal, while the wedge member 714 is moved in a direction L4a opposite to the fourth direction L4 by the driver 150 based on a drive signal. Thereby, the lens 710 of the second modification has a focal length that can be changed by the driver 150. In the above embodiments or the first modification, the lens 710 of the second modification can be used in place of the Alvarez lens 110.

(Third Modification)

In the above embodiments, as a method for changing a program to be executed by the controller, parameters (table information, threshold, etc.), or the like after the placement of the system in the eye, there are an invasive method and a non-invasive (low-invasive) method.

In the invasive method, for example, at least part of the intraocular lens system is taken out by surgery, or the intraocular lens system is directly manipulated in a predetermined manner by inserting an instrument into the eye to change the parameters, programs, or the like stored therein.

In the non-invasive method, for example, one or more switches, which are controlled in response to light such as laser light (or magnetic force, electromagnetic waves, etc.), are provided in the eye (e.g., on a surface of the controller or the first detector, etc.). The laser light is irradiated from the outside of the eye to thereby change the switching state of the switch(es). A signal is generated according to the switching state of the switch(es). The first detector and the controller receive the signal, and thus the table information, the threshold, the programs or the like is changed. The operation content of each switch can be changed by the laser intensity, the irradiation time, the irradiation pattern, or the like. When a plurality of switches is provided, the contents of their operations may be changed according to the selection of a switch to be operated or the order of switches to be operated.

The configurations described above are mere examples for embodying or carrying out the present invention, and therefore susceptible to several modifications and variations (omission, substitution, addition, etc.), all coming within the scope of the invention.

For example, the configuration of the lens according to the above embodiments or the modifications is not limited to those described in connection with FIG. 2 or 21. Besides, the driver of the above embodiments or the modifications is not limited to those described in connection with FIGS. 3 and 4. For example, the driver may be made of MEMS with the function of an actuator.

The transparent solar cell 130 and the non-transparent solar cell 230 are not limited to those described in the above embodiments or the modifications. For example, a dye-sensitized solar cell may be used as the transparent solar cell 130 or the non-transparent solar cell 230.

A computer program for realizing the above embodiments or the modifications may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The program may be sent/received through a network such as the Internet or LAN.

The invention claimed is:

1. An intraocular lens system, comprising:
a lens configured to be placed in an eye, transmit part of light incident on the eye therethrough, and have a variable focal length;
a converter configured to be placed in the eye posterior to the lens, and transmit part of the light transmitted through the lens to a cornea side of the converter therethrough while converting energy of an other part of the light transmitted through the lens to the cornea side of the converter into electrical energy;
a driver configured to be placed in the eye, and operate with the electrical energy received from the converter to change the focal length of the lens;
a retinal prosthesis configured to be placed in the eye, including a photoelectric conversion element array configured to operate with the electrical energy received from the converter to detect the light having transmitted through the converter to generate an electrical signal;
a transmitter configured to send the electrical signal generated by the retinal prosthesis for visual cortex of brain;
a controller configured to operate with the electrical energy received from the converter and control the driver, wherein the controller is configured to control the driver based on the electrical signal generated by the retinal prosthesis; and
an eye orientation detector configured to operate with the electrical energy received from the converter to detect orientation of the eye, wherein the controller is configured to control the driver based on a detection result obtained by the eye orientation detector.

2. The intraocular lens system according to claim 1, further comprising a ciliary body detector configured to be placed in the eye, and operate with the electrical energy received from the converter to detect movement of a ciliary body or a biological signal for moving the ciliary body,
wherein the driver is configured to change the focal length of the lens based on a detection result obtained by the ciliary body detector.

3. The intraocular lens system according to claim 2, wherein the ciliary body detector is configured to detect at least one of an acceleration of a predetermined portion of the ciliary body, a movement amount of a predetermined portion of the ciliary body, a tension of a ciliary zonule, and a myoelectric potential signal of a predetermined portion of the ciliary body.

4. The intraocular lens system according to claim 1, wherein
when the eye orientation detector detects that the eye is directed downward, the controller changes the focal length of the lens to a first focal length, and
otherwise, the controller changes the focal length of the lens to a second focal length that is longer than the first focal length.

5. The intraocular lens system according to claim 1, wherein the eye orientation detector is configured to detect at least one of an acceleration of a predetermined portion of the eye and a convergence eye movement.

6. The intraocular lens system according to claim 1, wherein the converter is provided with an opening to allow part of the light incident on the eye to pass therethrough.

7. The intraocular lens system according to claim 6, wherein the opening is formed in a position corresponding to a macula in the retinal prosthesis.

8. The intraocular lens system according to claim 6, wherein the photoelectric conversion element array is configured to receive the light having passed through the opening to generate the electrical signal.

9. The intraocular lens system according to claim 6, wherein the opening is provided with a lens configured to adjust a light flux that reaches a macula.

* * * * *